(12) United States Patent
Voytik-Harbin et al.

(10) Patent No.: US 8,084,055 B2
(45) Date of Patent: Dec. 27, 2011

(54) COLLAGEN PREPARATION AND METHOD OF ISOLATION

(75) Inventors: Sherry L. Voytik-Harbin, Zionsville, IN (US); Seth Kreger, New Richmond, IN (US); Brett Bell, Lafayette, IN (US); Jennifer Bailey, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/903,326

(22) Filed: Sep. 21, 2007

(65) Prior Publication Data
US 2008/0268052 A1    Oct. 30, 2008

Related U.S. Application Data

(60) Provisional application No. 60/846,207, filed on Sep. 21, 2006.

(51) Int. Cl.
*A61F 13/00* (2006.01)
(52) U.S. Cl. ...................................... 424/443
(58) Field of Classification Search ............... 424/443
See application file for complete search history.

(56) References Cited

U.S. PATENT DOCUMENTS

| | | | |
|---|---|---|---|
| 3,949,073 A | 4/1976 | Daniels et al. | |
| 4,233,360 A | 11/1980 | Luck et al. | |
| 4,544,516 A | 10/1985 | Hughes et al. | |
| 4,582,640 A | 4/1986 | Smestad et al. | |
| 4,789,663 A | 12/1988 | Wallace et al. | |
| 4,902,508 A | 2/1990 | Badylak et al. | |
| 4,956,178 A | 9/1990 | Badylak et al. | |
| 5,163,955 A | 11/1992 | Love et al. | |
| 5,204,382 A | 4/1993 | Wallace et al. | |
| 5,275,826 A | 1/1994 | Badylak et al. | |
| 5,281,422 A | 1/1994 | Badylak et al. | |
| 5,420,248 A | 5/1995 | Devictor et al. | |
| 5,460,962 A | 10/1995 | Kemp et al. | |
| 5,554,389 A | 9/1996 | Badylak et al. | |
| 5,885,619 A | 3/1999 | Patel et al. | |
| 5,948,429 A | 9/1999 | Bell et al. | |
| 5,955,110 A | 9/1999 | Patel et al. | |
| 6,099,567 A | 8/2000 | Badylak et al. | |
| 6,187,047 B1 | 2/2001 | Kwan et al. | |
| 6,206,931 B1 | 3/2001 | Cook et al. | |
| 6,264,992 B1 | 7/2001 | Voytik-Harbin et al. | |
| 6,375,989 B1 | 4/2002 | Badylak et al. | |
| 6,384,196 B1 | 5/2002 | Weis et al. | |
| 6,444,229 B2 | 9/2002 | Voytik-Harbin et al. | |
| 6,497,875 B1 | 12/2002 | Sorrell et al. | |
| 6,576,265 B1 | 6/2003 | Spievack | |
| 6,592,623 B1 | 7/2003 | Bowlin et al. | |
| 6,592,794 B1 | 7/2003 | Bachrach | |
| 6,666,892 B2 | 12/2003 | Hiles et al. | |
| 6,793,939 B2 | 9/2004 | Badylak | |
| 6,893,812 B2 | 5/2005 | Woltering et al. | |
| 2002/0076816 A1 | 6/2002 | Dai et al. | |
| 2002/0170120 A1 | 11/2002 | Eckmayer et al. | |
| 2002/0172705 A1 | 11/2002 | Murphy et al. | |
| 2004/0037813 A1 | 2/2004 | Simpson et al. | |
| 2004/0078076 A1 | 4/2004 | Badylak et al. | |
| 2004/0137616 A1 | 7/2004 | Isseroff et al. | |
| 2005/0014181 A1 | 1/2005 | Galis et al. | |
| 2005/0019419 A1 | 1/2005 | Badylak et al. | |
| 2005/0153442 A1 | 7/2005 | Katz et al. | |
| 2005/0226856 A1 | 10/2005 | Ahlfors | |
| 2005/0260748 A1 | 11/2005 | Chang et al. | |
| 2005/0266556 A1 | 12/2005 | Yoder et al. | |
| 2006/0147501 A1* | 7/2006 | Hillas et al. | 424/443 |
| 2006/0165667 A1 | 7/2006 | Laughlin et al. | |
| 2006/0235511 A1 | 10/2006 | Osborne | |
| 2007/0026518 A1 | 2/2007 | Healy et al. | |
| 2007/0077652 A1 | 4/2007 | Peled et al. | |
| 2007/0269476 A1 | 11/2007 | Voytik-Harbin et al. | |
| 2008/0025956 A1 | 1/2008 | Yoder et al. | |
| 2008/0199441 A1 | 8/2008 | Peled | |
| 2008/0268052 A1 | 10/2008 | Voytik-Harbin et al. | |
| 2009/0011021 A1 | 1/2009 | Voytik-Harbin et al. | |
| 2009/0069893 A1 | 3/2009 | Paukshto et al. | |
| 2009/0175922 A1 | 7/2009 | Voytik-Harbin et al. | |
| 2009/0280180 A1 | 11/2009 | Voytik-Harbin et al. | |

FOREIGN PATENT DOCUMENTS

| | | |
|---|---|---|
| DE | 201 15 753 U1 | 1/2002 |
| EP | 0443094 | 8/1991 |
| EP | 1264878 | 12/2002 |
| EP | 1 270 672 A1 | 1/2003 |
| EP | 1 674 116 A2 | 6/2006 |
| GB | 2366736 | 3/2002 |
| JP | 07 074239 B | 8/1995 |
| WO | WO 94/03119 | 2/1994 |
| WO | WO 01/23529 | 4/2001 |
| WO | WO 01/45765 | 6/2001 |
| WO | WO 02/102237 | 12/2002 |
| WO | WO 03/068287 | 8/2003 |
| WO | WO 03/071991 | 9/2003 |

(Continued)

OTHER PUBLICATIONS

International Search Report for International Application No. PCT/US07/020463, Feb. 21, 2008, 6 pgs.
Miller et al., "Preparation and Characterization of the Different Types of Collagen," *Methods in Enzymology*, 82: 33-64 (1982).
Nguyen et al., "Comparison of the Amino Acid Composition of Two Commercial Porcine Skins (Rind)," *Journal of Agricultural and Food Chemistry*, 34(3): 565-572 (1986).
Lin et al., "Comparison of Physical-Chemistry Properties of Type I Collagen from Different Species," *Food Chemistry*, 99(2): 244-251 (2005).

(Continued)

*Primary Examiner* — Maryam Monshipouri
(74) *Attorney, Agent, or Firm* — Barnes & Thornburg LLP

(57) ABSTRACT

Collagen compositions, methods for preparing those collagen compositions, and graft compositions formed from those collagen compositions are provided. In particular, methods of isolating collagen that exhibits an enhanced rate of polymerization and enhanced microstructural and mechanical properties upon polymerization, such collagen compositions, and graft compositions formed from such collagen compositions are provided.

24 Claims, 24 Drawing Sheets

FOREIGN PATENT DOCUMENTS

| WO | WO 03/087337 | | 10/2003 |
|---|---|---|---|
| WO | WO 03/097694 | | 11/2003 |
| WO | 2004/028404 | A2 | 4/2004 |
| WO | WO 2004/060426 | | 7/2004 |
| WO | 2004/078120 | * | 9/2004 |
| WO | WO 2006/003442 | | 1/2006 |
| WO | WO 2006/124946 | | 11/2006 |
| WO | WO 2006/125025 | | 11/2006 |
| WO | WO 2007/028079 | | 3/2007 |
| WO | WO 2007/136634 | | 11/2007 |
| WO | WO 2008/036393 | | 3/2008 |
| WO | WO 2009/076441 | | 6/2009 |
| WO | WO 2010/123928 | | 10/2010 |
| WO | WO 2011/009054 | | 1/2011 |

OTHER PUBLICATIONS

Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.

Comper, W. D., and A. Veis, "Characterization of Nuclei in in Vitro Collagen Fibril Formation", Biopolymers, vol. 16, 1977, pp. 2133-2142.

Bjornsson, S., "Simultaneous Preparation and Quantitation of Proteoglycans by Precipitation with Alcian Blue", Analytical Biochemistry, vol. 210, 1993, pp. 282-291.

Brightman, A. O., B. P. Rajwa, J. E. Sturgis, M. E. McCallister, J. P. Robinson, S. L. Voytik-Harbin, "Time-Lapse Confocal Reflection Microscopy of Collagen Fibrillogenesis and Extracellular Matrix Assembly in Vitro", Biopolymers, vol. 54, 2000, pp. 222-234.

Fulzele, S. V., P. M. Satturwar, A. K. Dorle, "Study of the Biodegradation and in Vivo Biocompatibility of Novel Biomaterials", European Journal of Pharmaceutical Sciences, vol. 20, 2003, pp. 53-61.

Gallop, P. M., and S. Seifter, "Preparation and Properties of Soluble Collagens", Soluble Collagens, 1963, pp. 635-641.

Griffey, S., N. D. Schwade, C. G. Wright, "Particulate Dermal Matrix as an Injectable Soft Tissue Replacement Material", J. Biomed. Mater. Res. vol. 58, 2001, pp. 10-15.

Hunt, T. K., P. Twomey, B. Zederfeldt, and J. E. Dunphy, "Respiratory Gas Tensions and PH in Healing Wounds", American Journal of Surgery, vol. 114, 1967, pp. 302-307.

Marotta, M., G. Martino, "Sensitive Spectrophotometric Method for the Quantitative Estimation of Collagen", Analytical Biochemistry, vol. 150, 1985, pp. 86-90.

Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.

Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.

Pizzo, A. M., K. Kokini, L. C. Vaughn, B. Z. Waisner, and S. L. Voytik-Harbin, "Extracellular Matrix (ECM) Microstructural Composition Regulates Local Cell-ECM Biomechanics and Fundamental Fibroblast Behavior: A Multidimensional Perspective", J. Appl. Physiol, vol. 98, 2005, pp. 1909-1921.

Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.

Voytik-Harbin, S. L., A. O. Brightman, B. Z. Waisner, J. P. Robinson, C. H. Lamar, "Small Intestinal Submucosa: A Tissue-Derived Extracellular Matrix That Promotes Tissue-Specific Growth and Differentiation of Cells in Vitro", Tissue Engineering, vol. 4, No. 2, 1998, pp. 157-174.

Voytik-Harbin, S. L., B. Rajwa, J. P. Robinson, "Three-Dimensional Imaging of Extracellular Matrix and Exttracellular Matrix-Cell Interactions", Methods in Cell Biology, vol. 63, 2001, pp. 583-597.

Bell, Brett J. et al., "Cell Density and Extracellular Matrix (ECM) Microstructure Control Mechanical Behavior of Engineered Tissue Constructs", 2005 Summer Bioengineering conference, (Jun. 22-26, 2005).

Callister, W. D. Jr. Materials Science and Engineering: an Introduction, $3^{rd}$ edition, New York, NY, John Wiley & Sons, Inc., 1994, Table of contents.

Davis, et al., "Injectable Self-Assembling Peptide Nanofibers Create Intramyocardial Microenvironments for Endothelial Cells", Circulation, 111, 442-50, (Feb. 1, 2005).

Hou, et al., "Radiolabeled Cell Distribution After Intramyocardial, Intracoronary, and Interstitial Retrograde Coronary Venous Delivery", Circulation, 112, 150-6, (Aug. 30, 2005).

Ingram, D. A., et al., "Identification of a Novel Hierarchy of Endothelial Progenitor Cells Using Human Peripheral and Umbilical Cord Blood", Blood, 104, 2752-2760, (2004).

Malvern Introduction to the Mechanics of a Continuous Medium. Upper Saddle River, NJ: Prentice-Hall, 1969, Table of contents and preface.

Narmoneva et al., "Endothelial Cells Promote Cardiac Myocyte Survival and Spatial Reorganization", Circulation, 110, 962-968, (Aug. 24, 2004).

Osborne, et al., "Investigation into the tensile properties of collagen/chondroitin-6-sulphate gels: the effect of crosslinking agents and diamines", Medical & Biological Engineering & Computing, vol. 36, 129-134, (1998).

Ozerdem, et al., "Physical Response of Collagen Gels to Tensile Strain", Journal of Biomechanical Engineering, vol. 117, 397-401, (Nov. 1995).

Pizzo et al., "Cell-Extracellular Matrix (ECM) Micro-Mechanical Behavior Depends on ECM Microstructure and Cell Type", 2005 Summer Bioengineering Conference, (Jun. 22-26, 2005).

Rehman, et al., "Secretion of Angiogenic and Antiapoptotic Factors by Human Adipose Stromal Cells", Circulation, 109: 1292-8, (Mar. 16, 2004).

Reinlib, et al., "Cell Transplantation as Future Therapy for Cardiovascular Disease?", Circulation, 101: e182-e187, (2000).

Roeder et al., "Local, Three-Dimensional Strain Measurements Within Largely Deformed Extracellular Matrix Constructs", J Biomech Eng, 126, 699-708, (2004).

Strang, et al., Linear Algebra and Its Applications. 3rd edition. San Diego, CA: Academic Press, 1988, Table of contents.

Veis, Arthur, et al., "Fundamentals of Interstitial Collagen Self-Assembly", 1994, Extracellular Matrix Assembly and Structure, Academic Press, pp. 15-45.

Voytik-Harbin et al., "Application and Evaluation of the Alamarblue Assay for Cell Growth and Survival of Fibroblasts", In Vitro Cell Dev Biol Anim, 34, 239-246, (1998).

Voytik-Harbin et al., "Simultaneous Mechanical Loading and Confocal Reflection Microscopy for Three-Dimensional Microbiomechanical Analysis of Biomaterials and Tissue Constructs", Microsc Microanal, 9, 74-85, (2003).

"Basement Membrane" accessed online at http://en.wikipedia.org/wiki/Basement_membrane#Composition on Jun. 11, 2010.

"Extracellular Matrix" accessed at http://en.wikipedia.org/wiki/Extracellular_matrix on Jun. 11, 2010.

Chandrakasan et al. J. Biol. Chem., 1976, 251:6062-67.

Ciovacco et al., Bone, 2009, 44(1):80-86.

Compston, "Bone marrow and bone: a functional unit," Journal of Endocrinology, 173: 387-394, 2002.

Gelman et al., "Collagen Fibril Formation in Vitro," J. Biol. Chem., 1979, 254(22): 11741-11745.

Gelman et al., "Collagen Fibril Formation," J. Biol. Chem., 1979, 254(1):180-186.

Kacena et al., J. of Histotechnology, 2004, 27:119-130.

Knott et al., "Collagen Cross-Links in Mineralizing Tissues: A Review of Their Chemistry, Function, and Clinical Relevance," 1998, 22(3):181-187.

Kondo et al., "Biology of Hematopoietic Stem Cells and Progenitors: Implications for Clinical Application," Annu. Rev. Immunol., 2003, 21:759-806.

Korff et al., Jour. of Cell Science, vol. 112: 3249-3258 (1999).

Kreger et al., "Hyaluronan concentration within a 3D collagen matrix modulates matrix viscoelasticity, but not fibroblast response," Matrix Biol., 2009, 28(6):336-46.

Kreger, "Design of 3D Collagen Matrices for Cell Delivery and Guidance in Tissue Engineering," Thesis Submitted to Purdue University in Partial Fulfillment of the Requirements for the Degree of Doctor of Philosophy, May 2009.

Na, "Monomer and Oligomer of Type I Collagen: Molecular Properties and Fibril Assembly," Biochemistry, 1989, 28(18):7161-67.

Orschell-Traycoff et al., Blood, 2000, 96:1380-1387.

Pizzo et al., "Long-term Production of Choline Acetylatransferase in the CNS After Transplantation of Fibroblasts Modified with a Regulatable Vector", *Mol Brain Res*, 126, 1-13 (2004).

Scadden, "The stem cell niche as an entity of action," Nature, 441: 1075-1079, 2006.

Schechner et al., "In vivo formation of complex microvessels lined by human endothelial cells in an immunodeficient mouse," *PNAS*, Aug. 1, 2000, vol. 97, No. 16, 9191-9196.

Shiozawa et al., "The bone marrow niche: habitat to hematopoietic and mesenchymal stem cells, and unwitting host to molecular parasites," Leukemia, 22(5): 941-950, 2008.

Sieminski et al., Expt. Cell Res., vol. 297, pp. 574-584 (2004).

Spradling et al., "Stem Cells Find Their Niche," Nature, 414, 2001.

Wess, Collagen fibrillar structure and hierarchies in P. Fratzl (ed.), Collagen: Structure and Mechanics, Springer Science + Business Media, LLC, New York, 2008, 53-60.

Yoder et al., "Redefining endothelial progenitor cells via clonal analysis and hematopoietic stem/progenitor cell principals," *Blood*, 2007, 109:1801-1809.

Bailey JL et al., "Collagen Oligomers Modulate Physical and Biological Properties of Three-Dimensional Self-Assembled Matrices," Biopolymers, 2010; 95(2): 77-93.

Na et al., "In Vitro Collagen Fibril Assembly in Glycerol Solution: Evidence for a Helical Cooperative Mechanism Involving Microfibrils," Biochemistry, 1986; 25: 958-966.

Na et al., "Mechanism of in Vitro Collagen Fibril Assembly," Journal of Biological Chemistry, 1986; 261(26): 12290-12299.

Voytik-Harbin et al., "Identification of Extractable Growth Factors from Small Intestine Submucosa," J Cell. Biochemistry, 1997; 67: 478-491.

Condell RA et al., "Analysis of Native Collagen Monomers and Oligomers by Size-Exclusion High-Performance Liquid Chromatography and its Application," Analytical Biochemistry, 1993; 212: 436-445.

Kim et al., "Characterization of Acid-soluble Collagen from Pacific Whiting Surimi Processing Byproducts", Journal of Food Science, vol. 69, No. 8, 2004, 6 pages.

"Density" form Merriam-Webster online, accessed on Feb. 1, 2011.

Munakata, et al., "Interaction between collagens and glycosaminoglycans investigated using a surface plasmon resonance biosensor", Glycobiology, vol. 9, 1023-1027 (1999).

* cited by examiner

FIGURE 1
COMPARISON OF PIG SKIN AND SIGMA COLLAGEN PREPS BY POLYACRYLAMIDE GEL ELECTROPHORESIS

4% NON-REDUCING GEL

LANE 1 MOLECULAR WEIGHT STANDARDS
LANE 2 PIG SKIN COLLAGEN(SK-LYOPHIL. RESUS. IN SAMPLE BUFFER)
LANE 3 PIG SKIN COLLAGEN(SK-LYOPHIL. RESUS. IN 0.01N HCL,NEUTRALIZED)
LANE 4 PIG SKIN COLLAGEN(PH-LYOPHIL. RESUS. IN 0.01N HCL,NEUTRALIZED)
LANE 5 BOVINE SIGMA COLLAGEN I(RESUS. IN 0.01N HCL, NEUTRALIZED)
LANE 6 BOVINE VITROGEN COLLAGEN I(IN 0.01N HCL, NEUTRALIZED)

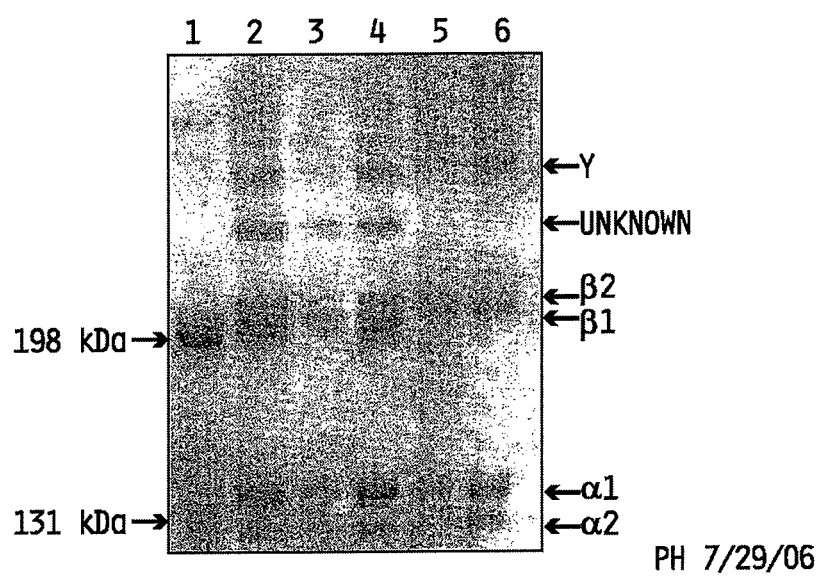

PH 7/29/06

COMPARISON OF POLYMERIZATION KINETICS OF PIG SKIN AND SIGMA COLLAGEN PREPS USING TURBIDITY ANALYSIS

FIGURE 3
COMPARISON OF MICROSTRUCTURE OF ENGINEERED ECMs PREPARED FROM PIG SKIN AND SIGMA COLLAGEN PREPS USING CONFOCAL REFLECTION MICROSCOPY
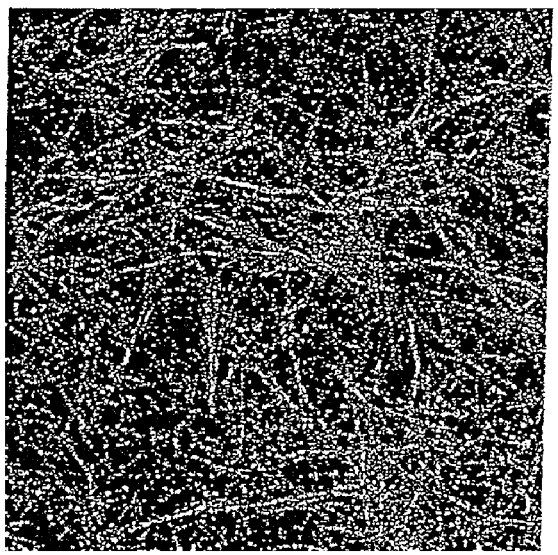
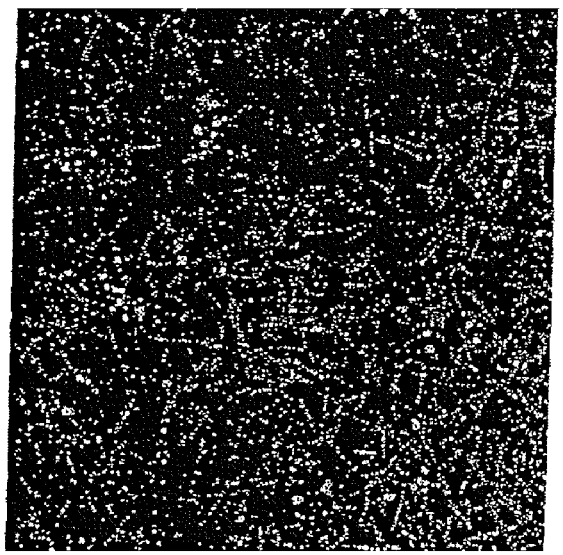
PIG SKIN COLLAGEN (1.5 mg/ml; 7-7-06 BATCH)
SIGMA COLLAGEN (1.5 mg/ml; 6-9-06 BATCH)

FIGURE 4
COMPARISON OF MICROSTRUCTURE OF ENGINEERED
ECMs PREPARED FROM PIG SKIN AND SIGMA COLLAGEN
PREPS USING SCANNING ELECTRON MICROSCOPY
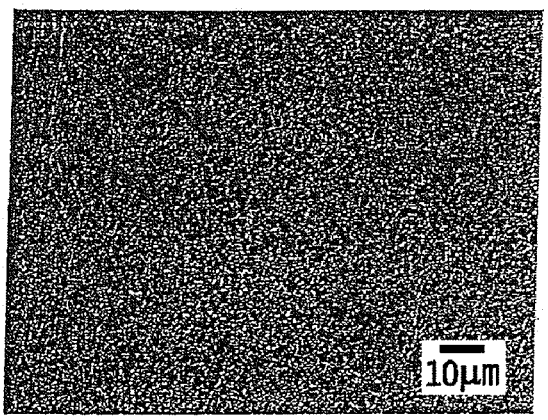
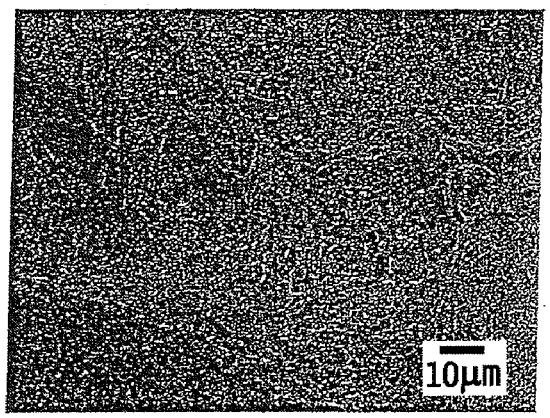
PIG SKIN COLLAGEN
(1 mg/ml; 7-7-06 BATCH)
SIGMA COLLAGEN
(1 mg/ml; 6-9-06 BATCH)
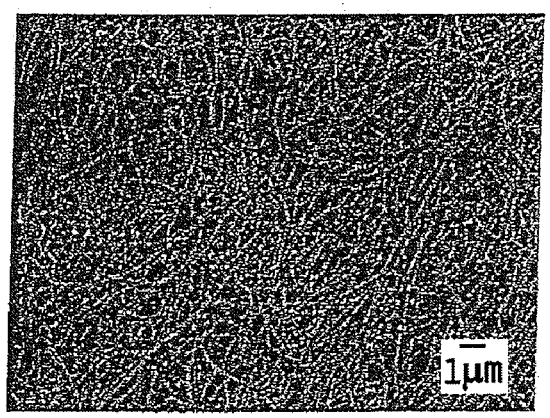
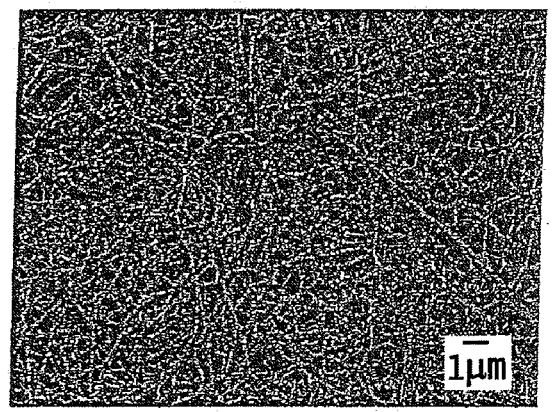

MECHANICAL BEHAVIOR OF ENGINEERED ECMs PREPARED WITH PIG SKIN AND SIGMA COLLAGENS IN UNCONFINED COMPRESSION

COMPARISON OF COLLAGEN PREPS BASED UPON SDS PAGE ANALYSIS OF CYANOGEN BROMIDE PEPTIDES

LANE 1 - LADDER
LANE 2 - COLLAGEN TYPE III
LANE 3 - COLLAGEN TYPE IV
LANE 4 - PIG COLLAGEN, 75 μg
LANE 5 - SIGMA COLLAGEN, 75 μg
LANE 6 - VITROGEN, 75 μg
LANE 7 - PIG COLLAGEN, 100 μg
LANE 8 - SIGMA COLLAGEN, 100 μg
LANE 9 - PIG COLLAGEN, UNDIGESTED
LANE 10 - SIGMA, UNDIGESTED

COLLAGEN PREPARATION AND METHOD OF ISOLATION

CROSS REFERENCE TO RELATED APPLICATIONS

This application claims priority under 35 U.S.C. §119(e) to U.S. Provisional Application Ser. No. 60/846,207, filed on Sep. 21, 2006, incorporated by reference herein in its entirety.

Research relating to this invention was supported in part by the U.S. Government under Grant No. EB000165 awarded from the National Institutes of Health. The U.S. Government has certain rights in this invention.

FIELD OF THE INVENTION

This invention relates to collagen compositions, methods for preparing those collagen compositions, and graft compositions formed from those collagen compositions. More particularly, the invention relates to methods of isolating collagen that exhibits an enhanced rate of polymerization and enhanced micro-structural and mechanical properties upon polymerization and to such collagen compositions and graft compositions formed from such collagen compositions.

BACKGROUND AND SUMMARY

The extracellular matrix (ECM) as it occurs in vivo plays a crucial role in the organization, homeostasis, and function of tissues and organs. Continuous communication between cells and their surrounding ECM environment orchestrates critical processes such as the acquisition and maintenance of differentiated phenotypes during embryogenesis, the development of form (morphogenesis), angiogenesis, wound healing, and even tumor metastasis. Both biochemical and biophysical signals from the ECM modulate fundamental cellular activities including adhesion, migration, proliferation, differential gene expression, and programmed cell death. The realization of the significance of the ECM to the organization, homeostasis, and function of tissues and organs has led to a renewed interest in characterizing ECM constituents and the relationship of these constituents to the functioning of the ECM.

ECMs, including various basement membrane tissues and other extracellular matrix tissues obtained from natural sources and matrices formed from isolated ECM components, can be utilized as tissue graft compositions for remodeling tissues in vivo or for in vitro applications. Complex scaffolds representing combinations of isolated extracellular matrix components in a natural or processed form are commercially available and can be used as tissue graft compositions (e.g., Human Extracellular Matrix (Becton Dickinson) and MATRIGEL®). Basement membrane tissues and other extracellular matrix tissues, such as tissue material derived from submucosal tissues, harvested from warm-blooded vertebrates have also shown great promise as unique graft materials for inducing the repair of damaged or diseased tissues in vivo, and for inducing the proliferation of cells in vitro.

In accordance with the invention, purified collagen can be used to produce an engineered ECM material prepared under conditions that regulate the polymerization of collagen in a controlled manner. This result is more difficult to achieve with existing intact or processed ECMs from natural sources and with ECMs and collagen preparations from commercial sources.

In the literature, there are known methods for isolating collagen from a variety of tissues, e.g., placenta, bladder, animal tails, and skin, and using the isolated material to reconstitute collagenous matrices. These collagenous matrices may have applications as graft materials for inducing the repair of damaged or diseased tissues in vivo, and for inducing the proliferation and other fundamental behavior of cells in vitro. The molecular forces that orchestrate the self assembly of soluble, monomeric collagen into higher ordered structures are weak so their assembly can easily turn into an unstructured aggregation of misfolded proteins. As reported herein, modifying the conditions used to isolate collagen results in collagen preparations with properties that enhance the rate at which the collagen polymerizes and that enhance the microstructural and mechanical properties of the collagen upon polymerization (e.g., the mechanical integrity of the engineered ECM that is formed upon collagen polymerization). The methods of collagen isolation and the collagen compositions described herein allow for the controlled alteration of the microstructural and subsequent mechanical properties of a resulting engineered ECM for such uses as graft compositions for inducing the repair of damaged or diseased tissues in vivo, and for inducing the proliferation and other fundamental behaviors of cells in vitro.

In one embodiment, a method for isolating collagen is provided. The method comprises the steps of obtaining a collagen-containing source material, comminuting the source material, mixing the comminuted source material with an extraction solution, extracting the comminuted source material to form a soluble fraction and an insoluble fraction, obtaining the insoluble fraction, extracting the collagen from the insoluble fraction to form a soluble collagen fraction, precipitating the collagen from the soluble collagen fraction, and resuspending the precipitate in an aqueous solution wherein the aqueous solution used to resuspend the collagen precipitate is an acidic solution. An isolated collagen composition prepared by this method is also provided.

In various embodiments of the embodiment described in the preceding paragraph: 1) the collagen-containing source material is selected from the group consisting of placental tissue, bladder tissue, intestinal tissue, alimentary tract tissue, ovarian tissue, pericardial tissue, animal tail tissue, liver tissue, skin tissue, and any other suitable collagen-containing source material, 2) the collagen-containing source material is selected from the group consisting of bladder tissue and skin tissue, 3) the collagen-containing source material is porcine skin tissue, 4) the source material is frozen in liquid nitrogen prior to the comminuting step, 5) the source material is frozen in liquid nitrogen during the comminuting step, 6) the source material is frozen in liquid nitrogen prior to and during the comminuting step, 7) the source material is frozen at a temperature of −20° C. or below prior to or during the comminuting step, 8) the source material is frozen at a temperature of −40° C. or below prior to or during the comminuting step, 9) the source material is frozen at a temperature of −60° C. or below prior to or during the comminuting step, 10) the source material is frozen at a temperature of −80° C. or below prior to or during the comminuting step, 11) the mixing step is performed by blending or stirring, 12) the mixing step is performed by stirring, 13) the soluble collagen fraction is not filtered between the step of extracting the collagen from the insoluble fraction to form the soluble collagen fraction and the step of precipitating the collagen from the soluble collagen fraction, 14) the method further comprises the step of lyophilizing the collagen precipitate, 15) the method further comprises the step of polymerizing the collagen prior to or after lyophilization, 16) the collagen is precipitated by dialysis against a buffered solution, and 17) the dialysis tubing has a molecular weight cut-off of about 12,000 to about 14,000. In an alternative embodiment, any of these steps can be used in any combination.

In one embodiment, a method for engineering matrices with enhanced polymerization characteristics is provided. The method comprises the steps of obtaining collagen oligomers, polymerizing the collagen oligomers, and forming the engineered matrices with enhanced polymerization characteristics. An engineered matrix prepared by this method is also provided.

In other embodiments, the enhanced polymerization characteristics are selected from the group consisting of an enhanced rate of polymerization, a reduced lag time for polymerization, and an enhanced mechanical integrity, and the enhanced mechanical integrity is selected from the group consisting of strength and stiffness. In yet another embodiment, the collagen oligomers polymerize with a maximal t ½ selected from the group consisting of about 3 minutes, about 2.5 minutes, about 2.0 minutes, about 1.5 minutes, and about 1 minute.

In other illustrative embodiments, the collagen oligomers are obtained by isolation from a collagen-containing source material that is a tissue naturally enriched with collagen oligomers, the collagen oligomers are obtained by isolating and then chemically cross-linking collagen, or the collagen oligomers are isolated from a diseased tissue or a genetically-modified tissue.

In still another embodiment, an engineered matrix is provided. The matrix comprises a predetermined percentage of collagen oligomers based on total isolated collagen used to make the engineered matrix. In various embodiments, the collagen is isolated from a tissue naturally enriched with collagen oligomers, the collagen oligomers are isolated from a diseased tissue or a genetically-modified tissue, or the collagen oligomers are obtained by isolating and then chemically cross-linking collagen. In another illustrative embodiment, the predetermined percentage of collagen oligomers is selected from the group consisting of about 0.5% to about 100%, about 1.0% to about 100%, about 2% to about 100%, about 3% to about 100%, about 5% to about 100%, about 10% to about 100%, about 15% to about 100%, about 20% to about 100%, about 30% to about 100%, about 40% to about 100%, about 50% to about 100%, about 60% to about 100%, about 70% to about 100%, about 80% to about 100%, about 90% to about 100%, about 95% to about 100%, and about 100%. In still another embodiment, the engineered matrix further comprises a predetermined percentage of isolated collagen monomers.

In another aspect, a graft composition is provided. The graft composition comprises an engineered matrix comprising collagen oligomers wherein the matrix has a predetermined percentage of collagen oligomers based on total isolated collagen used to make the engineered matrix. In one embodiment, the predetermined percentage of collagen oligomers is selected from the group consisting of about 0.5% to about 100%, about 1.0% to about 100%, about 2% to about 100%, about 3% to about 100%, about 5% to about 100%, about 10% to about 100%, about 15% to about 100%, about 20% to about 100%, about 30% to about 100%, about 40% to about 100%, about 50% to about 100%, about 60% to about 100%, about 70% to about 100%, about 80% to about 100%, about 90% to about 100%, about 95% to about 100%, and about 100%. In various embodiments, the collagen oligomers are isolated from a diseased tissue or a genetically-modified tissue, the collagen oligomers are obtained by isolating and then chemically cross-linking collagen, or the collagen oligomers are isolated from a natural tissue enriched with collagen oligomers. In yet another embodiment, the graft composition further comprises a predetermined percentage of collagen monomers based on total isolated collagen used to make the engineered matrix.

Surprisingly, the inclusion of increased amounts of collagen oligomers in a collagen composition may increase the rate of polymerization, facilitate hierarchical assembly of component collagen fibrils, and enhance mechanical properties (e.g., strength and stiffness).

BRIEF DESCRIPTION OF THE DRAWINGS

FIG. 1 shows a polyacrylamide gel electrophoresis comparison of collagen isolated from pig skin, using the methods described herein, and a commercially available collagen preparation.

FIG. 3 shows a comparison using confocal reflection microscopy of the microstructure of an engineered ECM prepared from pig skin collagen, using the methods described herein, and a commercially available collagen preparation.

FIG. 4 shows a comparison using scanning electron microscopy of the microstructure of an engineered ECM prepared from pig skin collagen, using the methods described herein, and a commercially available collagen preparation.

FIG. 10A shows the SDS-PAGE gel and FIG. 10B shows the corresponding densitometry analysis.

FIG. 24A shows microstructural analysis of engineered ECMs using confocal reflection microscopy (fibril density vs. collagen concentration). FIG. 24B shows microstructural analysis of engineered ECMs using confocal reflection microscopy (average fibril diameter vs. collagen concentration).

DETAILED DESCRIPTION OF THE ILLUSTRATIVE EMBODIMENTS

Figure 2:
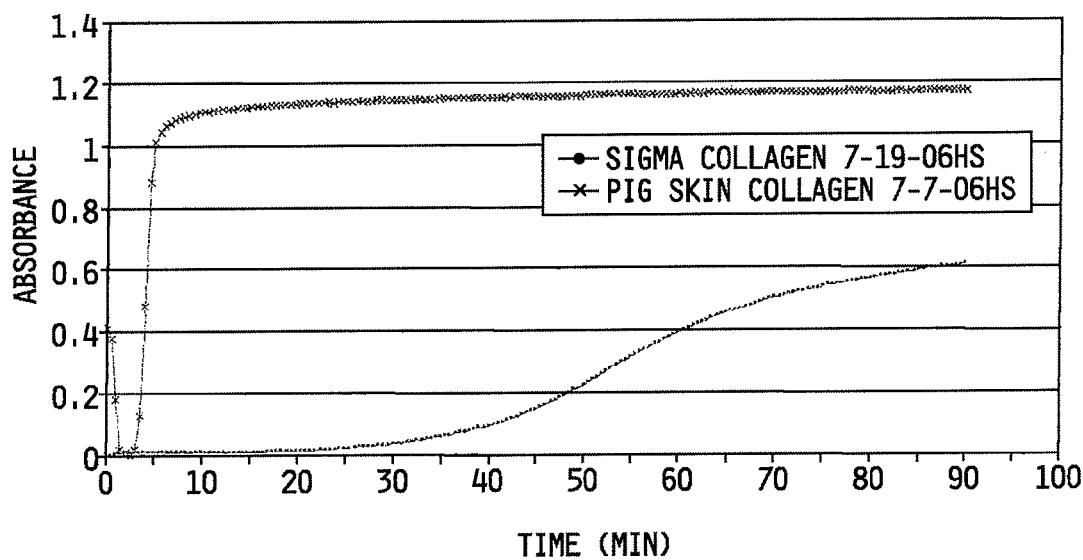
FIG. 2 shows a comparison by using turbidity analysis of the kinetics of polymerization of collagen isolated from pig skin using the methods described herein and a commercially available collagen preparation.

As used herein, the term "lyophilized" means that water is removed from the composition, typically by freeze-drying under a vacuum. However, lyophilization can be performed by any method known to the skilled artisan and the method is not limited to freeze-drying under a vacuum.

As used herein "collagen-based matrix" means a matrix that comprises collagen. In illustrative embodiments, the "collagen-based matrices" described herein can be engineered from isolated collagen.

As used herein "engineered matrix" means a collagen-based matrix that is polymerized under conditions that are systematically varied where the conditions are selected from the group consisting of, but not limited to, pH, phosphate concentration, temperature, buffer composition, ionic strength, and composition and concentration of collagen.

As used herein, "isolated collagen" means any type of collagen, naturally present in a collagen-containing source material (described below) wherein the collagen has been at least partially purified by isolation and removal from the collagen-containing source material.

As used herein "sterilization" or "sterilize" or "sterilized" means removing unwanted contaminants including, but not limited to, endotoxins, nucleic acid contaminants, and infectious agents.

As used herein collagen "oligomer(s)" means covalently cross-linked collagen monomers (e.g., dimers=2 monomers, trimers=3 monomers, etc.).

The present invention relates to a method of preparing a collagen-based matrix. In one illustrative embodiment, methods for isolating collagen and then preparing the collagen-based matrix are provided. The method for isolating collagen comprises the steps of obtaining a collagen-containing source material, comminuting the source material, mixing the comminuted source material with an extraction solution, extracting the comminuted source material to form a soluble fraction and an insoluble fraction, obtaining the insoluble fraction, extracting the collagen from the insoluble fraction to form a soluble collagen fraction, precipitating the collagen from the soluble collagen fraction, and resuspending the precipitate in an aqueous solution wherein the aqueous solution used to resuspend the collagen precipitate is an acidic solution. In additional embodiments, the isolated collagen can be precipitated by dialysis against a buffered solution, for example, using dialysis tubing with a molecular weight cut-off of about 12,000 to about 14,000. In yet another embodiment, the isolated collagen can be lyophilized after precipitation.

In another illustrative aspect, a polymerizing step can be performed under conditions that are systematically varied where the conditions are selected from the group consisting of pH, phosphate concentration, temperature, buffer composition, ionic strength, the specific isolated collagen components present, and the concentration of the isolated collagen components present. In one illustrative embodiment, the isolated collagen can be lyophilized prior to polymerization. The isolated collagen can be lyophilized in an acid, such as acetic acid, hydrochloric acid, formic acid, lactic acid, citric acid, sulfuric acid, ethanoic acid, carbonic acid, nitric acid, or phosphoric acid. In still another embodiment, the isolated collagen can be polymerized after precipitation, and optionally, the engineered matrix that results can be lyophilized.

In another illustrative embodiment, the invention relates to a collagen-based matrix prepared using the methods described above. In various embodiments, the collagen-based matrix can contain fibrils with specific characteristics, including, but not limited to, a fibril area fraction or a fibril volume fraction (i.e., density) of about 0.1% to about 100%, about 0.5% to about 100%, about 0.5% to about 26%, about 1% to about 100%, about 1% to about 26%, about 1% to about 7%, about 1% to about 15%, about 7% to about 26%, about 20% to about 30%, about 20% to about 50%, about 20% to about 70%, and about 20% to about 100%, about 30% to about 50%, about 30% to about 70%, and about 30% to about 100% and/or a modulus (e.g., an elastic or linear modulus, a compressive modulus, or a shear storage modulus) of about 0.5 kPa to about 40 kPa, about 30 kPa to 100 kPa, about 30 kPa to about 1000 kPa, about 30 kPa to about 10000 kPa, about 30 kPa to about 70000 kPa, about 100 kPa to 1000 kPa, about 100 kPa to about 10000 kPa, and about 100 kPa to about 70000 kPa.

Exemplary of tissues useful as a collagen-containing source material for isolating collagen to make the collagen-based matrices described herein are submucosa tissues or any other extracellular matrix-containing tissues of a warm-blooded vertebrate. Exemplary methods of preparing submucosa tissues are described in U.S. Pat. Nos. 4,902,508; 5,281,422; and 5,275,826, each incorporated herein by reference. Extracellular matrix material-containing tissues other than submucosa tissue may be used in accordance with the methods and compositions described herein. Methods of preparing other extracellular matrix material-derived tissues are known to those skilled in the art. For example, see U.S. Pat. Nos. 5,163,955 (pericardial tissue); 5,554,389 (urinary bladder submucosa tissue); 6,099,567 (stomach submucosa tissue); 6,576,265 (extracellular matrix tissues generally); 6,793,939 (liver basement membrane tissues); and U.S. patent application publication no. US-2005-0019419-A1 (liver basement membrane tissues); and international publication no. WO 2001/45765 (extracellular matrix tissues generally), each incorporated herein by reference. In various other embodiments, the collagen-containing source material can be selected from the group consisting of placental tissue, ovarian tissue, animal tail tissue, and skin tissue (e.g., see Example 1 and Gallop, et al., Preparation and Properties of Soluble Collagens, *Meth. Enzymol.* 6: 635-641 (1963), incorporated herein by reference). Any suitable extracellular matrix-containing tissue can be used as a collagen-containing source material.

In one illustrative embodiment, the extracellular matrix material-derived tissues used as the collagen-containing source material can be derived from a vertebrate tissue material comprising submucosa. In various embodiments, vertebrate tissue material comprising submucosa can be obtained from intestinal tissue harvested from animals raised for meat production, including, for example, pigs, cattle and sheep or other warm-blooded vertebrates. In various aspects, the tissue material comprising submucosa can be obtained from intestine, stomach, urinary bladder, the uterus, and any other submucosa-containing tissue.

An illustrative preparation method for tissue material comprising submucosa is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells. In this embodiment, the tissue material comprising submucosa is rinsed under hypotonic conditions, such as with water or with saline under hypotonic conditions and is optionally sterilized. In another illustrative embodiment, such compositions can be prepared by mechanically removing the luminal portion of the tunica mucosa and the external muscle layers and/or lysing resident cells with hypotonic washes, such as water or saline under hypotonic conditions. In these embodiments, the tissue material comprising submucosa can be stored in a hydrated or dehydrated state prior to extraction. In various aspects, the tissue material comprising submucosa can comprise any delamination embodiment, including the tunica submucosa delaminated from both the tunica muscularis and at least the luminal portion of the tunica mucosa of a warm-blooded vertebrate.

In various embodiments, the isolated collagen can also contain glycoproteins, proteoglycans, glycosaminoglycans (e.g., chondroitins and heparins), etc. extracted from the insoluble fraction with the collagen. The engineered matrices prepared by the methods described herein can serve as matrices for the regrowth of endogenous tissues at the implantation site (e.g., biological remodeling) which can assume the characterizing features of the tissue(s) with which they are associated at the site of implantation, insertion, or injection.

In various illustrative embodiments, the collagen-containing source material, the isolated collagen, or the collagen-based matrix, including an engineered matrix, can be disinfected and/or sterilized using conventional sterilization techniques including glutaraldehyde tanning, formaldehyde tanning at acidic pH, propylene oxide or ethylene oxide treatment, gas plasma sterilization, gamma radiation, electron beam, and/or peracetic acid sterilization. Sterilization techniques which do not adversely affect the structure and biotropic properties of the source material or the collagen can be used. Illustrative sterilization techniques are exposing the collagen-containing source material, the isolated collagen, or the collagen-based matrix, including an engineered matrix, to peracetic acid, 1-4 Mrads gamma irradiation (or 1-2.5 Mrads of gamma irradiation), ethylene oxide treatment, or gas plasma sterilization. In one embodiment, the collagen-containing source material, the isolated collagen, or the collagen-based matrix, including an engineered matrix, can be subjected to one or more sterilization processes. In an illustrative embodiment, peracetic acid can be used for sterilization.

Typically, prior to extraction, the collagen-containing source material is comminuted by tearing, cutting, grinding, or shearing the collagen-containing source material. In one illustrative embodiment, the collagen-containing source material can be comminuted by shearing in a high-speed blender, or by grinding the collagen-containing source material in a frozen state (e.g., at a temperature of −20° C., −40° C., −60° C., or −80° C. or below prior to or during the comminuting step) and then lyophilizing the material to produce a powder having particles ranging in size from about 0.1 mm$^2$ to about 1.0 mm$^2$. In one illustrative embodiment, the collagen-containing source material is comminuted by freezing and pulverizing under liquid nitrogen in an industrial blender. In this embodiment, the collagen-containing source material can be frozen in liquid nitrogen prior to, during, or prior to and during the comminuting step.

In one illustrative embodiment, after comminuting the collagen-containing source material, the material is mixed (e.g., by blending or stirring) with an extraction solution to extract and remove soluble proteins. Illustrative extraction solutions include sodium acetate (e.g., 0.5 M and 1.0 M). Other exemplary methods for extracting soluble proteins are known to those skilled in the art and are described in detail in U.S. Pat. No. 6,375,989, incorporated herein by reference. Illustrative extraction excipients include, for example, chaotropic agents such as urea, guanidine, sodium chloride or other neutral salt solutions, magnesium chloride, and non-ionic or ionic surfactants.

In one illustrative aspect, after the initial extraction, the soluble fraction can be separated from the insoluble fraction to obtain the insoluble fraction. For example, the insoluble fraction can be separated from the soluble fraction by centrifugation (e.g., 2000 rpm at 4° C. for 1 hour). In alternative embodiments, other separation techniques known to those skilled in the art, such as filtration, can be used. In one embodiment, the initial extraction step can be repeated one or more times, discarding the soluble fractions. In another embodiment, after completing the extractions, one or more steps can be performed of washing with water the insoluble fraction, followed by centrifugation, and discarding of the supernatant where the water is the supernatant.

In accordance with one illustrative embodiment, the insoluble fraction can then be extracted (e.g., with 0.075 M sodium citrate) to obtain the isolated collagen. In illustrative aspects the extraction step can be repeated multiple times retaining the soluble fractions. In one embodiment, the accumulated soluble fractions can be combined and can be clarified to form the soluble fraction, for example by centrifugation (e.g., 2000 rpm at 4° C. for 1 hour).

In one embodiment, the soluble fraction can be fractionated to precipitate the isolated collagen. In one illustrative aspect, the soluble fraction can be fractionated by dialysis. Exemplary molecular weight cut-offs for the dialysis tubing or membrane are from about 3,500 to about 12,000 or about 3,500 to about 5,000 or about 12,000 to about 14,000. In various illustrative embodiments, the fractionation, for example by dialysis, can be performed at about 2° C. to about 37° C. for about 1 hour to about 96 hours. In one embodiment, the soluble fraction is dialyzed against a buffered solution (e.g., 0.02 M sodium phosphate dibasic). However, the fractionation can be performed at any temperature, for any length of time, and against any suitable buffered solution. In one embodiment, the precipitated collagen is then collected by centrifugation (e.g., 2000 rpm at 4° C. for 1 hour). In another embodiment, after precipitation, one or more steps can be performed of washing the precipitate with water, followed by centrifugation, and discarding of the supernatant where the water is the supernatant.

In various illustrative embodiments, the precipitated collagen can then be resuspended in an aqueous solution wherein the aqueous solution is acidic. For example, the aqueous acidic solution can be an acetic acid solution, but any other acids including hydrochloric acid, formic acid, lactic acid, citric acid, sulfuric acid, ethanoic acid, carbonic acid, nitric acid, or phosphoric acid can be used. For example, acids, at concentrations of from about 0.001 N to about 0.1 N, from about 0.005 N to about 0.1 N, from about 0.01 N to about 0.1 N, from about 0.05 N to about 0.1 N, from about 0.001 N to about 0.05 N, from about 0.001 N to about 0.01 N, or from about 0.01 N to about 0.05 N can be used to resuspend the precipitate.

As discussed above, the term "lyophilized" means that water is removed from the composition, typically by freeze-drying under a vacuum. In one illustrative aspect, the isolated resuspended collagen can be lyophilized after it is resuspended. In another illustrative embodiment, the polymerized matrix itself can be lyophilized. In one illustrative lyophilization embodiment, the resuspended collagen is first frozen, and then placed under a vacuum. In another lyophilization embodiment, the resuspended collagen can be freeze-dried under a vacuum. In another lyophilization embodiment, the precipitated collagen can be lyophilized before resuspension. Any method of lyophilization known to the skilled artisan can be used.

In additional embodiments, the acids described above can be used as adjuvants for storage after lyophilization in any combination. The acids that can be used as adjuvants for storage include hydrochloric acid, acetic acid, formic acid, lactic acid, citric acid, sulfuric acid, ethanoic acid, carbonic acid, nitric acid, or phosphoric acid, and these acids can be used at any of the above-described concentrations. In one illustrative embodiment, the lyophilizate can be stored (e.g., lyophilized in and stored in) an acid, such as acetic acid, at a concentration of from about 0.001 N to about 0.5 N or from about 0.01 N to about 0.5 N. In another embodiment, the lyophilizate can be stored in water with a pH of about 6 or below. In another embodiment, the lyophilized product can be stored dry. In other illustrative embodiments, lyoprotectants, cryoprotectants, lyophilization accelerators, or crystallizing excipients (e.g., ethanol, isopropanol, mannitol, trehalose, maltose, sucrose, tert-butanol, and tween 20), or combinations thereof, and the like can be present during lyophilization.

In accordance with one illustrative embodiment, the resuspended collagen is sterilized. Exemplary sterilizing and/or disinfecting agents are described above, but any sterilizing and/or disinfecting agent or method of sterilization known in the art can be used. The resuspended collagen can be sterilized using chloroform, glutaraldehyde, formaldehyde, acidic pH, propylene oxide, ethylene oxide, gas plasma sterilization, gamma radiation, electron beam sterilization, or peracetic acid sterilization, or combinations thereof, and the like. Illustrative sterilization techniques are exposing the resuspended collagen to peracetic acid, 1-4 Mrads gamma irradiation (or 1-2.5 Mrads of gamma irradiation), ethylene oxide treatment, or gas plasma sterilization.

In one embodiment, the isolated collagen can be sterilized before lyophilization. In another illustrative embodiment the isolated collagen can be sterilized after lyophilization or the collagen-containing source material can be sterilized. Sterilization of the collagen-containing source material can be performed, for example, as described in U.S. Pat. Nos. 4,902,508 and 6,206,931, incorporated herein by reference. In another illustrative embodiment, the polymerized matrix formed from the isolated collagen is sterilized.

In one illustrative embodiment, the isolated collagen is directly sterilized after resuspension, for example, with peracetic acid or with peracetic acid and ethanol (e.g., by the addition of 0.18% peracetic acid and 4.8% ethanol to the resuspended collagen solution before lyophilization). In another embodiment, sterilization can be carried out during the fractionation step. For example, the isolated collagen composition can be dialyzed against chloroform, peracetic acid, or a solution of peracetic acid and ethanol to disinfect or sterilize the isolated collagen. Illustratively, the isolated collagen can be sterilized by dialysis against a solution of peracetic acid and ethanol (e.g., 0.18% peracetic acid and 4.8% ethanol). The chloroform, peracetic acid, or peracetic acid/ethanol can be removed prior to lyophilization, for example by dialysis against an acid, such as 0.01 N acetic acid. In an alternative embodiment, the lyophilized composition can be sterilized directly after rehydration, for example, by the addition of 0.18% peracetic acid and 4.8% ethanol. In this embodiment, the sterilizing agent can be removed prior to polymerization of the isolated collagen to form fibrils.

If the isolated collagen or polymerized collagen is lyophilized, the lyophilized composition can be stored frozen, refrigerated, or at room temperature (for example, at about −80° C. to about 25° C.). Storage temperatures are selected to stabilize the collagen. The compositions can be stored for about 1-26 weeks, or longer.

In one embodiment, the isolated collagen can be dialyzed against 0.01 N acetic acid, for example, prior to lyophilization to remove the sterilization solution and so that the isolated collagen is in a 0.01 N acetic acid solution. In another embodiment, the isolated collagen can be dialyzed against hydrochloric acid, for example, prior to lyophilization and can be lyophilized in hydrochloric acid and redissolved in hydrochloric acid, acetic acid, or water.

If the isolated collagen is lyophilized, the resulting lyophilizate can be redissolved in any solution, but may be redissolved in an acidic solution or water. In various aspects, the lyophilizate can be redissolved in, for example, acetic acid, hydrochloric acid, formic acid, lactic acid, citric acid, sulfuric acid, ethanoic acid, carbonic acid, nitric acid, or phosphoric acid, at any of the above-described concentrations, or can be redissolved in water. In one illustrative embodiment the lyophilizate is redissolved in 0.01 N acetic acid. For use in producing engineered matrices that can be injected in vivo or used for other purposes in vitro, the redissolved lyophilizate can be subjected to varying conditions (e.g., pH, phosphate concentration, temperature, buffer composition, ionic strength, and composition and concentration of the isolated collagen components (dry weight/ml)) that result in polymerization to form engineered matrices for specific tissue graft applications.

For use in producing engineered matrices that can be 1.) injected in vivo and used for specific tissue graft applications or 2.) used for other purposes in vitro, such as studying cell-extracellular matrix interactions, the isolated collagen can be subjected to varying conditions for polymerization to form fibrils. In illustrative embodiments, the conditions that can be varied include pH, phosphate concentration, temperature, buffer composition, ionic strength, the particular isolated collagen components (e.g., type I and type III collagen) and other ECM components present, and the concentration of the isolated collagen (dry weight/ml). These conditions result in polymerization of the isolated collagen to form engineered matrices with desired compositional, microstructural, and mechanical characteristics. Illustratively, these compositional, microstructural, and mechanical characteristics can include fibril length, fibril diameter, number of fibril-fibril connections (e.g., cross-links), fibril density, fibril organization, matrix composition, 3-dimensional shape or form, and viscoelastic, tensile, shear, or compressive behavior (e.g., failure stress, failure strain, and modulus), permeability, degradation rate, swelling, hydration properties (e.g., rate and swelling), and in vivo tissue remodeling and bulking properties, rate of polymerization, lag time of polymerization, extent of polymerization, viscosity of interstitial fluid and desired in vitro and in vivo cell responses. The collagen-based matrices described herein have desirable biocompatibility and in vitro and in vivo remodeling properties, among other desirable properties.

In various illustrative embodiments, qualitative and quantitative microstructural characteristics of the engineered matrices can be determined by environmental or cryostage scanning electron microscopy, transmission electron microscopy, confocal microscopy, second harmonic generation multi-photon microscopy. In another embodiment, polymerization kinetics may be determined by spectrophotometry or time-lapse confocal reflection microscopy. In another embodiment, tensile, compressive and viscoelastic properties can be determined by rheometry or tensile testing. In another embodiment, a rat subcutaneous injection model can be used to determine remodeling properties. All of these methods are known in the art or are further described in the Examples or are described in Roeder et al., *J. Biomech. Eng.*, vol. 124, pp. 214-222 (2002), in Pizzo et al., *J. Appl. Physiol.*, vol. 98, pp. 1-13 (2004), Fulzele et al., *Eur. J. Pharm. Sci.*, vol. 20, pp. 53-61 (2003), Griffey et al., *J. Biomed. Mater. Res.*, vol. 58, pp. 10-15 (2001), Hunt et al., *Am. J. Surg.*, vol. 114, pp. 302-307 (1967), and Schilling et al., *Surgery*, vol. 46, pp. 702-710 (1959), incorporated herein by reference.

In accordance with one embodiment, the isolated collagen is polymerized to form fibrils at a final concentration (dry weight/ml) of about 0.05 to about 5.0 mg/ml of the isolated collagen, or in another embodiment the final concentration is selected from the range of about 0.05 mg/ml to about 4.0 mg/ml, and in another embodiment the final concentration is selected from the range of about 0.05 mg/ml to about 3.0 mg/ml, and in another embodiment the final concentration is about 0.05, 0.1, 0.2, 0.3, 0.5, 1.0, 2.0, or 3.0 mg/ml. In other embodiments, the isolated collagen is polymerized at final concentrations (dry weight/ml) of about 5 to about 10 mg/ml, about 5 to about 30 mg/ml, about 5 to about 50 mg/ml, about 5 to about 100 mg/ml, about 20 to about 50 mg/ml, about 20 to about 60 mg/ml, or about 20 to about 100 mg/ml.

In various illustrative embodiments, the polymerization reaction is conducted in a buffered solution using any biologically compatible buffer known to those skilled in the art. For example, the buffer may be selected from the group consisting of phosphate buffer saline (PBS), Tris(hydroxymethyl)aminomethane Hydrochloride (Tris-HCl), 3-(N-Morpholino) Propanesulfonic Acid (MOPS), piperazine-n,n'-bis (2-ethanesulfonic acid) (PIPES), [n-(2-Acetamido)]-2-Aminoethanesulfonic Acid (ACES), N-[2-hydroxyethyl] piperazine-N'-[2-ethanesulfonic acid] (HEPES), and 1,3-bis [tris(Hydroxymethyl)methylamino]propane (Bis Tris Propane). In one embodiment the buffer is PBS, Tris, or MOPS and in one embodiment the buffer system is PBS.

In various illustrative embodiments, the polymerization of the isolated collagen is conducted at a pH selected from the range of about 5.0 to about 11, and in one embodiment polymerization is conducted at a pH selected from the range of about 6.0 to about 9.0, and in one embodiment polymerization is conducted at a pH selected from the range of about 6.5 to about 8.5, and in another embodiment the polymerization of the isolated collagen is conducted at a pH selected from the range of about 7.0 to about 8.5, and in another embodiment the polymerization of the isolated collagen is conducted at a pH selected from the range of about 7.3 to about 7.4.

In other illustrative aspects, the ionic strength of the buffered solution is also regulated. In accordance with one embodiment, the ionic strength of the buffer used to polymerize the isolated collagen is selected from a range of about 0.05 to about 1.5 M, in another embodiment the ionic strength is selected from a range of about 0.10 to about 0.90 M, in another embodiment the ionic strength is selected from a range of about 0.14 to about 0.30 M and in another embodiment the ionic strength is selected from a range of about 0.14 to about 0.17 M.

In still other illustrative embodiments, the polymerization is conducted at temperatures selected from the range of about 0° C. to about 60° C. In other embodiments, the polymerization is conducted at temperatures above 20° C., and typically the polymerization is conducted at a temperature selected from the range of about 20° C. to about 40° C., and more typically the temperature is selected from the range of about 30° C. to about 40° C. In one illustrative embodiment the polymerization is conducted at about 37° C.

In yet other embodiments, the phosphate concentration is varied. For example, in one embodiment, the phosphate concentration is selected from a range of about 0.005 M to about 0.5 M. In another illustrative embodiment, the phosphate concentration is selected from a range of about 0.01 M to about 0.2 M. In another embodiment, the phosphate concentration is selected from a range of about 0.01 M to about 0.1 M. In another illustrative embodiment, the phosphate concentration is selected from a range of about 0.01 M to about 0.03 M.

In other illustrative embodiments, the isolated collagen can be polymerized by, for example, extrusion into a desired buffer, including the buffers described above, or wet-spinning to form strands of isolated collagen. In one embodiment the strands can be formed by extrusion through a needle and can be air-dried to form fibers or threads of various dimensions. The syringe can be adapted with needles or tubing to control the dimensions (e.g., diameter) of the fibers or threads. In one embodiment, the extrusion process involves polymerization of the isolated collagen followed by extrusion into a bath containing water, a buffer, or an organic solvent (e.g., ethanol). In another embodiment, the extrusion process involves coextrusion of the isolated collagen with a polymerization buffer (e.g., the buffer such as Tris or phosphate buffers at various concentrations can be varied to control pH and ionic strength). In yet another embodiment, the extrusion process involves extrusion of the isolated collagen into a polymerization bath (e.g., the buffer such as Tris or phosphate buffers at various concentrations can be varied to control pH and ionic strength). The bath conditions affect polymerization time and properties of the fibers or threads, such as mechanical integrity of the fibers or threads, fiber dimensions, and the like. In one embodiment, the fibers can be air-dried to create materials suitable for use as sutures. Multiple fibers can be assembled (e.g., woven, braided to form matrix constructs).

In various embodiments, the engineered matrices of the present invention can be combined, prior to, during, or after polymerization, with nutrients, including minerals, amino acids, sugars, peptides, proteins, vitamins (such as ascorbic acid), or glycoproteins that facilitate cellular proliferation, such as laminin and fibronectin, hyaluronic acid, or growth factors such as epidermal growth factor, platelet-derived growth factor, transforming growth factor beta, or fibroblast growth factor, and glucocorticoids such as dexamethasone. In other illustrative embodiments, fibrillogenesis inhibitors, such as glycerol, glucose, or polyhydroxylated compounds can be added prior to or during polymerization. In accordance with one embodiment, cells can be added to the isolated collagen as the last step prior to the polymerization or after polymerization of the engineered matrix. In another illustrative embodiment, particulate extracellular matrix material can be added to the isolated collagen and can enhance bulking capacity. In other illustrative embodiments, cross-linking agents, such as carbodiimides, aldehydes, lysl-oxidase, N-hydroxysuccinimide esters, imidoesters, hydrazides, and maleimides, and the like can be added before, during, or after polymerization.

The isolated collagen is derived from a collagen-containing source material and, in some embodiments, may contain glycoproteins, such as laminin and fibronectin, proteoglycans, such as serglycin, versican, decorin, and perlecan, and glycosaminoglycans. In one embodiment, the isolated collagen can be further purified or partially purified and the purified or partially purified composition can be used in accordance with the methods described herein or mixtures of partially purified or purified components can be used. As used herein, the term "purified" means the isolation of collagen in a form that is substantially free from other components (e.g., typically the total amount of other components present in the composition represents less than 5%, or more typically less than 0.1%, of total dry weight).

In additional illustrative embodiments, engineered matrices are provided. The engineered matrices can be prepared according to the methods described herein, including any of the methods or conditions for polymerization described herein. The engineered matrices comprise collagen fibrils. As used herein the term "collagen fibril" refers to a quasi-crystalline, filamentous structure formed by the self-assembly of soluble collagen molecules. The engineered matrices comprise collagen fibrils which may pack in a quarter-staggered pattern giving the fibril a characteristic striated appearance or banding pattern along its axis. Collagen fibrils are distinct from the amorphous aggregates or precipitates of insoluble collagen that can be formed by dehydrating (e.g., lyophilizing) collagen suspensions to form porous network scaffolds.

Typically, the matrices are prepared from isolated collagen at collagen concentrations ranging from about 0.05 to about 5.0 mg/ml, about 1.0 mg/ml to about 3.0 mg/ml, about 0.05 mg/ml to about 10 mg/ml, about 0.05 to about 20 mg/ml, about 0.05 to about 30 mg/ml, about 0.05 to about 40 mg/ml, about 0.05 to about 50 mg/ml, about 0.05 to about 60 mg/ml, about 0.05 to about 80 mg/ml, about 5 mg/ml to 10 mg/ml, about 5 mg/ml to 20 mg/ml, about 5 mg/ml to about 40 mg/ml, about 5 mg/ml to 60 mg/ml, about 5 mg/ml to about 100 mg/ml, about 20 mg/ml to about 40 mg/ml, about 20 mg/ml to 60 mg/ml, or about 20 mg/ml to about 100 mg/ml.

In another illustrative embodiment, the engineered matrices contain fibrils with specific characteristics, including, but not limited to, a fibril area fraction (defined as the percent area of the total area occupied by fibrils in a cross-sectional surface of the matrix; 2-dimensional) or a fibril volume fraction (the percent area of the total area occupied by fibrils in 3 dimensions) of about 0.1% to about 100%, about 0.5% to about 100%, about 0.5% to about 26%, about 1% to about 100%, about 1% to about 26%, about 1% to about 7%, about 1% to about 15%, of about 7% to about 26%, about 20% to about 30%, about 20% to about 50%, about 20% to about 70%, about 20% to about 100%, about 30% to about 50%, about 30% to about 70%, or about 30% to about 100%.

In yet another embodiment, the three-dimensional engineered matrices have a modulus (e.g., an elastic or linear modulus (defined by the slope of the linear region of the stress-strain curve obtained using conventional mechanical testing protocols; i.e., stiffness), a compressive modulus, or a shear storage modulus) of about 0.5 kPa to about 40 kPa, about 30 kPa to 100 kPa, about 30 kPa to about 1000 kPa, about 30 kPa to about 10000 kPa, about 30 kPa to about 70000 kPa, about 100 kPa to 1000 kPa, about 100 kPa to about 10000 kPa, or about 100 kPa to about 70000 kPa.

In another embodiment the engineered matrices have a fibril area fraction or a fibril volume fraction of about 0.5% to about 1%, about 0.5% to about 5%, 0.5% to about 10%, about 0.5% to about 50%, about 0.5% to about 100%, or of about 7% to about 26%. In another embodiment the engineered matrices have a fibril area fraction or a fibril volume fraction of about 7% to about 15% or about 16% to about 26%. In another embodiment the engineered matrices have a fibril area fraction or a fibril volume fraction of about 18.5% to about 25%. In another embodiment the engineered matrices are formed from collagen at concentrations of about 3.2, 3.4, 3.6, 3.8, 4.0, 4.5 or 5.0 mg/ml of collagen, resulting in engineered matrices having a fibril area fraction of about 19%, 19.7%, 20.5%, 21.2%, 22%, 23.8% and 25.6%, respectively.

In yet another embodiment, the engineered matrices have a modulus of about 0.5 to about 40 kPa. In accordance with another embodiment, the engineered matrices have a relatively low modulus of about 0.5 to about 24.0 kPa. In one other embodiment, the engineered matrices have a relatively high modulus of about 25 to about 40 kPa.

In illustrative embodiments, as discussed above, the polymerization reaction for engineered matrices can be conducted in a buffered solution using any biologically compatible buffer system known to those skilled in the art. For example, the buffer may be selected from the group consisting of phosphate buffer saline (PBS), Tris (hydroxymethyl)aminomethane Hydrochloride (Tris-HCl), 3-(N-Morpholino) Propanesulfonic Acid (MOPS), piperazine-n,n'-bis(2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES) and 1,3-bis[tris (Hydroxymethyl)methylamino]propane (Bis Tris Propane). In one embodiment the buffer is PBS, Tris, or MOPS and in one embodiment the buffer system is PBS, and more particularly 10×PBS. In accordance with one embodiment, the 10×PBS buffer at pH 7.4 comprises the following ingredients:

1.37 M NaCl
0.027 M KCl
0.081 M $Na_2HPO_4$
0.015 M $KH_2PO_4$
5 mM $MgCl_2$
55.5 mM glucose In one embodiment, to create 10×PBS buffers of different pH's, the ratio of $Na_2HPO_4$ and $KH_2PO_4$ is varied. In another embodiment, ionic strength may be adjusted as an independent variable by varying the molarity of NaCl only.

In accordance with one embodiment, for polymerization to form the engineered matrices, the isolated collagen can be pipetted into a plate with wells and the isolated collagen can be allowed to polymerize under any of the conditions described above. For example, a humidified environment at 37° C. for approximately 30 minutes can be used. In an alternative embodiment, the isolated collagen is injected into a host and is polymerized in vivo.

As discussed above, in accordance with one embodiment, cells can be added to the isolated collagen as the last step prior to the polymerization. In another embodiment, cells can be added after polymerization of the engineered matrix. The engineered matrices comprising the cells can be subsequently injected or implanted in a host for use as a tissue graft. In another embodiment, the cells on or within the engineered matrix can be cultured in vitro, for a predetermined length of time, to increase the cell number or to induce desired remodeling prior to implantation or injection into a host. In a further embodiment, the cells can be cultured in vitro, for a predetermined length of time, to increase cell number and the cells can be separated from the matrix and implanted or injected into the host in the absence of the engineered matrix.

In still another illustrative embodiment, the engineered matrices can include exogenous glucose and/or calcium chloride in the interstitial fluid of the matrices to promote cell growth. In one embodiment, about 1.0 mM to about 300 mM glucose and about 0.2 mM to about 4.0 mM $CaCl_2$ is included. In one embodiment, the isolated collagen comprises about 0.1 mg/ml to about 3 mg/ml total isolated collagen in about 0.05 to about 0.005N HCl, about 0.07M to about 0.28M NaCl, about 1.3 to about 4.5 mM KCl, about 4.0 to about 16 mM $Na_2HPO_4$, about 0.7 to about 3.0 mM $KH_2PO_4$, about 0.25 to about 1.0 mM $MgCl_2$, and about 2.77 mM to about 166.5 mM glucose. In this embodiment, polymerization of the isolated collagen is induced by the addition of a neutralizing solution such as NaOH. For example, a NaOH solution can be added to a final concentration of 0.01N NaOH. In this embodiment, cells are then added and a calcium chloride solution is also added to bring the final concentration of $CaCl_2$ to about 0.4 mM to about 2.0 mM $CaCl_2$. The composition is then allowed to polymerize either in vitro or in vivo to form an engineered matrix comprising collagen fibrils with cells in and/or on the matrix.

In accordance with one embodiment, a kit is provided for preparing engineered matrices. In this embodiment, the kit comprises sterilized components that can be combined to form an engineered matrix comprising collagen fibrils. In one embodiment, cells may constitute a component of the kit. In accordance with one embodiment, the kit comprises an isolated collagen composition, and a polymerization composition. In one embodiment, the kit comprises separate vessels, each containing one of the following components: isolated collagen, a phosphate buffer solution, a glucose solution, a calcium chloride solution, and a basic neutralizing solution. In one embodiment, the isolated collagen is provided in a lyophilized form and the kit is further provided with a solution of acetic acid (or other dilute acid including for example, hydrochloric acid, formic acid, lactic acid, citric acid, sulfuric acid, ethanoic acid, carbonic acid, nitric acid, or phosphoric acid) for resuspending the lyophilized isolated collagen.

In another embodiment, the kit comprises a solution comprising isolated collagen, a phosphate buffer solution, a glucose solution, a calcium chloride solution, an acid solution, and a basic neutralizing solution. In another embodiment, the kit can include isolated collagen and a polymerization buffer. In one embodiment the polymerization composition comprises a phosphate buffer that has a pH of about 7.2 to about 7.6 and the acid solution is an acetic acid solution comprising about 0.05N to about 0.005N acetic acid. In another embodiment, the acid solution is about 0.01N acetic acid. In another embodiment the polymerization composition comprises a phosphate buffer that has a pH of about 7.2 to about 7.6 and the acid solution is a hydrochloric acid solution comprising about 0.05N to about 0.005N hydrochloric acid. In another embodiment, the acid solution is about 0.01N hydrochloric acid. In one embodiment, the glucose solution has a concentration selected from the range of about 0.2% to about 5% w/v glucose, or about 0.5% to about 3% w/v glucose, and in one embodiment the glucose solution is about 1% w/v glucose. In one embodiment the $CaCl_2$ solution has a concentration selected from the range of about 2 mM to about 40.0 mM $CaCl_2$ or about 0.2 mM to about 4.0 mM $CaCl_2$, or about 0.2 to about 2 mM $CaCl_2$. In one embodiment the kit is provided with a 10×PBS buffer having a pH of about pH 7.4, and comprising about 1.37M NaCl, about 0.027M KCl, about 0.081M $Na_2HPO_4$, about 0.015M $KH_2PO_4$, about 5 mM $MgCl_2$ and about 1% w/v glucose. In another embodiment, kits are provided that comprise three-dimensional, preformed engineered matrices prepared according to any of the methods described herein and wherein the kits comprise any of the components described herein.

The kits can further comprise instructional materials describing methods for mixing the kit reagents to prepare engineered matrices or describing methods for using preformed, three-dimensional engineered matrices. In particular, the instructional materials can provide information regarding the final concentrations that give optimal microenvironmental conditions including fibril microstructure and mechanical properties for a particular cell type or for a particular desired result.

The lyophilized isolated collagen prepared by the methods described herein maintains its bioactivity (i.e., the capacity to polymerize and form fibrils in vitro or in vivo and to remodel tissue in vivo). In one embodiment, the isolated collagen can be used, for example, for making engineered matrices for specific tissue graft applications. In another embodiment, the lyophilized isolated collagen is useful commercially for the mass production of isolated collagen (i.e., the components can be lyophilized and stored without loss of bioactivity) for use in making engineered matrices. Lyophilized, isolated collagen that retains bioactivity and polymerization capacity is also useful for the concentration of isolated collagen for preparing engineered matrices that require concentration (i.e., higher concentrations) of collagen.

Surprisingly, the inclusion of increased amounts of isolated collagen oligomers in a collagen composition may increase the rate of polymerization, decrease lag time, facilitate hierarchical assembly of component collagen fibrils, and enhance mechanical properties (e.g., strength and stiffness). Accordingly, in one embodiment, a collagen composition is provided comprising collagen oligomers wherein the oligomers are isolated from a mammalian tissue enriched with or containing collagen oligomers.

In another illustrative embodiment, a method for engineering matrices with enhanced polymerization characteristics is provided. The method comprises the steps of obtaining collagen oligomers, polymerizing the collagen oligomers, and forming the engineered matrices with enhanced polymerization characteristics. In another aspect, the enhanced polymerization characteristics are selected from the group consisting of an enhanced rate of polymerization, a reduced lag time for polymerization, and an enhanced mechanical integrity. In another embodiment, the enhanced mechanical integrity is selected from the group consisting of strength and stiffness. In another embodiment, the polymerization characteristics are enhanced relative to type I isolated collagen obtained from Sigma-Aldrich as described in Example 2 and polymerized under the conditions described in Example 3. In still another embodiment, the collagen oligomers polymerize with a maximal T ½ of 3 minutes, 2.5 minutes, 2.0 minutes, 1.5 minutes, or 1 minute.

In yet another embodiment, the collagen-containing source material enriched with collagen oligomers is a tissue naturally enriched with collagen oligomers. In other embodiments, the collagen-containing source material enriched with collagen oligomers is a diseased tissue or a genetically-modified tissue where the tissue is enriched with collagen oligomers. In another illustrative aspect, the collagen-containing source material enriched with collagen oligomers is a mechanically-modified tissue or an electrically-modified tissue. In another embodiment, the collagen-containing source material is mechanically modified cultured cells or electrically-modified cultured cells. In still another aspect, the collagen oligomers are obtained by isolating and then chemically cross-linking collagen.

Extracellular matrix materials can be utilized as tissue graft compositions for remodeling tissues in vivo or for in vitro applications. The methods of collagen isolation and the collagen compositions described herein allow for the controlled alteration of the microstructural and subsequent mechanical properties of a resulting engineered matrix for such uses as graft compositions for inducing the repair of damaged or diseased tissues in vivo, and for inducing the proliferation or other fundamental behaviors of cells in vitro. Systematic variation of engineered matrix design features using the methods of polymerization described herein provides control of in vivo (e.g., cell infiltration, vascularization, rate of cell proliferation, differentiation, morphogenesis, remodeling, degradation, and contractility) and in vitro (e.g., cell morphology, migration, proliferation, differentiation, morphogenesis, and contractility) responses.

Accordingly, in another embodiment a graft composition comprising an engineered matrix comprising collagen oligomers is provided. The graft composition has a predetermined percentage of collagen oligomers based on total isolated collagen added to make the engineered matrix. In various embodiments, the predetermined percentage of collagen oligomers can be about 0.5% to about 100%, about 1% to about 100%, about 2% about 100%, about 3% to about 100%, about 5% to about 100%, about 10% to about 100%, about 15% to about 100%, about 20% to about 100%, about 30% to about 100%, about 40% to about 100%, about 50% to about 100%, about 60% to about 100%, about 70% to about 100%, about 80% to about 100%, about 90% to about 100%, about 95% to about 100%, or about 100%. In yet another embodiment, the collagen oligomers are obtained from a collagen-containing source material enriched with collagen oligomers (e.g., pig skin). In other embodiments, the collagen-containing source material enriched with collagen oligomers is a natural tissue, a diseased tissue or a genetically-modified tissue where the tissue is enriched with collagen oligomers. In still another aspect, the graft composition comprises collagen oligomers obtained by isolating and then chemically cross-linking collagen.

In another embodiment, the polymerization characteristics of the engineered matrix used to make the graft composition are enhanced relative to type I isolated collagen obtained from Sigma-Aldrich as described in Example 2 and polymerized under the conditions described in Example 3. In still another embodiment, the collagen oligomers that polymerize to form the engineered matrix polymerize with a maximal T ½ of 3 minutes, 2.5 minutes, 2.0 minutes, 1.5 minutes, or 1 minute.

All of the disclosure herein of methods of isolation of collagen, methods of polymerization of isolated collagen to form engineered matrices, the use of those engineered matrices in graft compositions, and disclosure relating to isolated collagen compositions and graft compositions, applies equally to isolated collagen enriched with collagen oligomers. In one illustrative embodiment, isolated collagen enriched with oligomers can be prepared by isolating collagen from a natural tissue (e.g., pig skin) according to the methods described herein. In one embodiment, the collagen oligomers can be isolated by a method such as the method described in Example 10. In other embodiments, oligomer-monomer separation can be achieved using methods that vary polymerization reaction parameters including temperature, pH, and ionic strength. Any other method known to the skilled artisan to be useful for separating collagen oligomers and monomers can be used.

In accordance with one embodiment, a kit is provided for preparing engineered matrices. In this embodiment, the kit comprises sterilized components that can be combined to form an engineered matrix comprising collagen fibrils. In one embodiment, the sterilized components include isolated collagen oligomers. In one embodiment, cells may constitute a component of the kit. In accordance with one embodiment, the kit comprises an isolated collagen oligomer composition, and a polymerization composition. In one embodiment, the kit comprises separate vessels, each containing one of the following components: isolated collagen oligomers, a phosphate buffer solution, a glucose solution, a calcium chloride solution, and a basic neutralizing solution. In another embodiment, the kit comprises separate vessels, each containing one of the following components: isolated collagen oligomers, isolated collagen monomers, a phosphate buffer solution, a glucose solution, a calcium chloride solution, and a basic neutralizing solution. In one embodiment, the isolated collagen is provided in a lyophilized form and the kit is further provided with a solution of acetic acid (or other dilute acid including for example, hydrochloric acid, formic acid, lactic acid, citric acid, sulfuric acid, ethanoic acid, carbonic acid, nitric acid, or phosphoric acid) for resuspending the lyophilized isolated collagen oligomers or monomers.

In another embodiment, the kit comprises a solution comprising isolated collagen oligomers and/or monomers, a phosphate buffer solution, a glucose solution, a calcium chloride solution, an acid solution, and a basic neutralizing solution. In another embodiment, the kit can comprise isolated collagen and a polymerization buffer. In one embodiment the polymerization composition comprises a phosphate buffer that has a pH of about 7.2 to about 7.6 and the acid solution is an acetic acid solution comprising about 0.05N to about 0.005N acetic acid. In another embodiment, the acid solution is about 0.01N acetic acid. In one embodiment the polymerization composition comprises a phosphate buffer that has a pH of about 7.2 to about 7.6 and the acid solution is a hydrochloric acid solution comprising about 0.05N to about 0.005N hydrochloric acid. In another embodiment, the acid solution is about 0.01N hydrochloric acid. In one embodiment, the glucose solution has a concentration selected from the range of about 0.2% to about 5% w/v glucose, or about 0.5% to about 3% w/v glucose, and in one embodiment the glucose solution is about 1% w/v glucose. In one embodiment the $CaCl_2$ solution has a concentration selected from the range of about 2 mM to about 40.0 mM $CaCl_2$ or about 0.2 mM to about 4.0 mM $CaCl_2$, or about 0.2 to about 2 mM $CaCl_2$. In one embodiment the kit is provided with a 10×PBS buffer having a pH of about pH 7.4, and comprising about 1.37M NaCl, about 0.027M KCl, about 0.081M $Na_2HPO_4$, about 0.015M $KH_2PO_4$, about 5 mM $MgCl_2$ and about 1% w/v glucose. In another embodiment, kits are provided that comprise three-dimensional, preformed engineered matrices prepared according to any of the methods described herein, including engineered matrices formed from isolated collagen oligomers alone, or isolated collagen oligomers and monomers in predetermined percentages of total collagen used to form the matrix, and wherein the kits comprise any of the components described herein.

The kits can further comprise instructional materials describing methods for mixing the kit reagents to prepare engineered matrices or describing methods for using preformed, three-dimensional engineered matrices. In particular, the instructional materials can provide information regarding the final concentrations that give optimal microenvironmental conditions including fibril microstructure and mechanical properties for a particular cell type or for a particular desired result.

The following examples illustrate specific embodiments in further detail. These examples are provided for illustrative purposes only and should not be construed as limiting the invention or the inventive concept in any way.

Example 1

Collagen Isolation

To prepare collagen, skin was harvested from pig immediately following euthanasia and was washed thoroughly with cold water. The skin was stretched out and pinned to a board and stored at 4° C. The hair was removed with clippers. The dermal layer of the tissue was isolated by separating and removing the upper epidermal layer and the lower loose fatty connective layers. This removal was readily achieved by scraping the tissue with a knife or straight razor. The tissue was maintained at 4° C.

The resulting dermal layer tissue was washed in water and then cut into small pieces (approximately 1 cm2) and was frozen and stored at −80° C. The frozen skin pieces were pulverized under liquid nitrogen using an industrial blender or cryogenic grinder. Soluble proteins were removed by extracting the pig skin powder (0.125 g/ml) with 0.5M sodium acetate overnight at 4° C. The resulting mixture was then centrifuged at 2000 rpm (700×g) at 4° C. for 1 hour. The supernatant was discarded and the extraction procedure repeated three additional times.

The resulting pellet was then suspended (0.25 g/ml) in cold MilliQ water and then centrifuged at 2000 rpm (700×g) at 4° C. for 1 hour. The pellet was then washed with water two additional times. Collagen extraction was then performed by suspending the pellet (0.125 g/ml) in 0.075M sodium citrate. The extraction was allowed to proceed for 15-18 hours at 4° C.

The resulting mixture was centrifuged at 2000 rpm (700×g) at 4° C. for 1 hour. The supernatant was retained and stored at 4° C. The pellet was re-extracted with 0.075M sodium citrate. The extraction process was repeated such that the tissue was extracted a total of three times. The resulting supernatants were then combined and centrifuged at 9750 rpm (17,000×g) at 4° C. for 1 hour to clarify the solution. The supernatant was retained and the pellet discarded.

Collagen was then precipitated from the supernatant by dialyzing (MWCO 12-14,000) extensively against 0.02 M disodium hydrogen phosphate at 4° C. The resulting suspension was then centrifuged at 2000 rpm at 4° C. for 1 hour and the pellet retained. The pellet was then resuspended and rinsed in cold MilliQ water. The suspension was centrifuged at 2000 rpm at 4° C. for 1 hour. The water rinse procedure was repeated two additional times.

The resulting collagen pellet was dissolved in 0.1M acetic acid and then lyophilized. The lyophilized material was stored within a dessicator at 4° C. for use in engineering ECMs.

Example 2

Polyacrylamide Gel Electrophoresis

Interrupted gel electrophoresis was performed to compare the protein composition of the collagen preparations made in accordance with the methods described herein to commercially available type I isolated collagen obtained from Sigma-Aldrich, St. Louis, Mo. (Sigma Cat. No. C3511) and pepsin-solubilized collagen from INAMED (Fremont, Calif.) sold under the product name PureCol™. Interrupted gel electrophoresis was performed according to Sykes, et al. The estimation of two collagens from human dermis by interrupted gel electrophoresis. *Biochem. Biophys. Res. Commun.* 72:1472-1480 (1976), incorporated herein by reference. Sodium dodecylsulfate polyacryamide gel electrophoresis (SDS-PAGE) was performed according to the method of Nielsen, et al. Measurements of molecular weights by gel electrophoresis. *Methods in Enzymology*, vol. 48, Hirs and Temasheff, Eds., Academic Press, New York, pp. 3-11 (1978), incorporated herein by reference.

The evaluation by SDS-PAGE of the protein composition of the collagen preparations made in accordance with the methods described herein indicates that the protocol yielded a pure type I collagen preparation (see below) with minimal to no contaminating non-collagenous proteins (see lanes 2-4 of the gel shown in FIG. 1). The gel shown in FIG. 1 indicates the band pattern of the α1, α2, β11, and β12 chains of collagen. No significant glycosaminoglycan content was identified using a standard alcian blue assay (Bjornsson, S. Simultaneous preparation and quantitation of proteoglycans by precipitation with alcian blue. *Anal Biochem.* 210:282-291 (1993), incorporated herein by reference).

Figure 6:
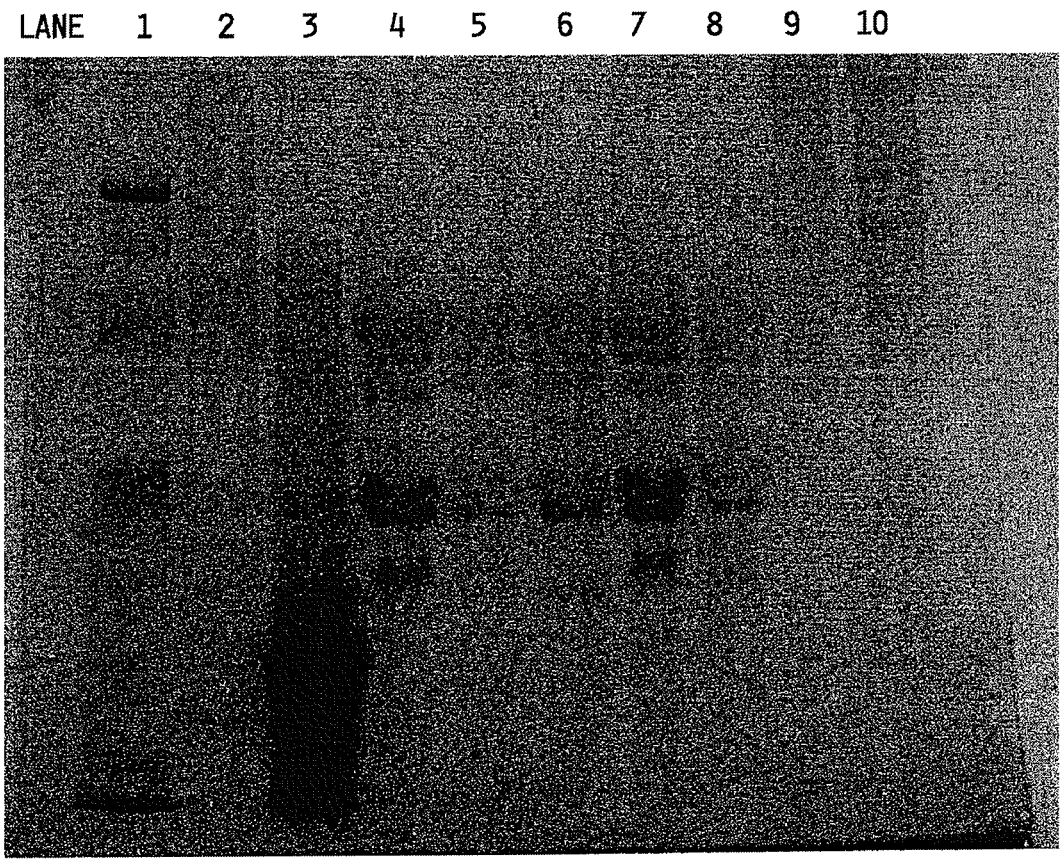
FIG. 6 shows a polyacrylamide gel electrophoresis comparison of cyanogen bromide peptides from collagen isolated from pig skin collagen, using the methods described herein, and commercially available collagen preparations.

Cyanogen bromide (CNBr) peptide analysis was used to confirm the presence of type I collagen in the pig skin collagen preparation (lanes 2-4), made according to the methods described herein. CNBr peptide analysis was performed according to the method of Miller, et al. Identification of three genetically distinct collagens by cyanogen bromide cleavage of insoluble skin and cartilage collagen. *Biochem. Biophys. Res. Commun.* 42:1024-1029 (1971). Standard SDS-PAGE within 12% gels was then performed to compare the CNBr-derived peptides from the various collagen preparations (see FIG. 6). The pattern shown in FIG. 6 indicates that the pig skin collagen preparation, made in accordance with the methods described herein, has a number of bands which are similar to Sigma collagen and INAMED collagen. However, there are also bands specific to the pig skin collagen composition. The presence of type I collagen was confirmed in the preparation described herein, and the preparation described herein does not have significant amounts of type V collagen or type III collagen (confirmed using interrupted gel electrophoresis). Types III and V collagen are the other two major types of collagen found in skin.

As also shown in FIG. 1, the pig skin type I collagen preparation (lanes 2-4), made according to the methods described herein, yielded a distinct collagen banding pattern compared to the commercially available collagen preparations, namely Sigma Type I collagen (acid solubilized; lane 5) and INAMED collagen (acid/pepsin solubilized; lane 6). Surprisingly, differences between the collagen preparations made in accordance with the methods described herein and the Sigma and INAMED collagen preparations were observed. As noted in FIG. 1 (band designated "Unknown"), a unique high molecular weight protein band was identified within the pig skin collagen preparation made in accordance with the methods described herein. The band was not observed in the INAMED or Sigma commercially available collagen preparations. The unknown protein band was also isolated, digested with CNBr, and a banding pattern indicative of collagen alpha chains was found.

Example 3

Polymerization Kinetics

The polymerization kinetics of the pig skin collagen preparation made in accordance with the methods described herein were also compared to commercially available Sigma Type I collagen. For this evaluation a spectrophotometric turbidity analysis assay for determining polymerization kinetics of collagen, well-known to those skilled in the art was used. The assay was performed in accordance with Comper, et al. Characterization of nuclei in in vitro collagen fibril formation. *Biopolymers* 16:2133-2142 (1977) and Brightman, et al. Time-lapse confocal reflection microscopy of collagen fibrillogenesis and extracellular matrix assembly in vitro. *Biopolymers* 54:222-234 (2000), each incorporated herein by reference. The time-course of polymerization was monitored in a Lambda 35 UV-VIS spectrophotometer (Perkin-Elmer) equipped with a temperature-controlled, 8-position cell changer as described previously by Brightman et al., 2000.

FIG. 2 shows the time-dependent changes in absorbance as recorded at a wavelength of 405 nm as each of the collagen preparations (each at 2 mg/ml collagen concentration as determined using sirius red analysis) underwent polymerization or fibrillogenesis (i.e., soluble state to an insoluble fibrillar state). The sirius red assay was performed in accordance with Marotta, et al. Sensitive spectrophotometric method for the quantitative estimation of collagen. *Anal. Biochem.* 150: 86-90 (1985), incorporated herein by reference. The pig skin collagen preparation made in accordance with the methods described herein showed a decreased lag time, increased polymerization rate, and increased magnitude of change in A405 readings. Surprisingly, the pig skin collagen preparation made in accordance with the methods described herein exhibited a much decreased lag time and increased polymerization rate in comparison to commercially available Sigma Type I collagen.

Example 4

Microstructure Comparison Using Confocal Reflection Microscopy

The collagen fibril microstructure of a 3D ECM engineered from pig skin collagen, prepared in accordance with the methods described herein, and from commercially available Sigma Type I collagen were determined and compared using confocal reflection microscopy. Each collagen composition was polymerized at 1.5 mg/ml. Confocal Reflection Microscopy was performed according to Brightman, et al. Time-lapse confocal reflection microscopy of collagen fibrillogenesis and extracellular matrix assembly in vitro. *Biopolymers* 54:222-234 (2000) and Voytik-Harbin, et al. Three-dimensional imaging of extracellular matrix and extracellular matrix-cell interactions. *Methods in Cell Biology* 63:583-597 (2001), each incorporated herein by reference.

Briefly, for example, solutions of collagen were polymerized in a Lab-Tek chambered coverglass and imaged using a BioRad Radiance 2100 MP Rainbow confocal/multiphoton microscope using a 60×1.4 NA oil immersion lens (or an Olympus Fluoview FV 1000 confocal microscope was used). Optical settings were established and optimized for matrices after polymerization was complete. Samples were illuminated with 488 nm laser light and the reflected light detected with a photomultiplier tube (PMT) using a blue reflection filter.

The fibril microstructure produced by the pig skin collagen, prepared in accordance with the methods described herein, showed an increase in fibril density and, surprisingly, an apparent increase in fibril-to-fibril association (e.g., cross-linked and/or fibril aggregates; see FIG. 3A (pig skin collagen preparation)) and 3B (commercially available Sigma Type I collagen)).

Example 5

Microstructure Comparison Using Scanning Electron Microscopy

The collagen fibril microstructure of a 3D ECM engineered from pig skin collagen, prepared in accordance with the methods described herein, and from commercially available Sigma Type I collagen were determined and compared using scanning electron microscopy. Each collagen composition was polymerized at 1.0 mg/ml. The fibril microstructures produced by the pig skin collagen, prepared in accordance with the methods described herein, showed a different appearance than the commercially available Sigma Type I collagen. FIGS. 4A and B show pig skin collagen, prepared in accordance with the methods described herein, and FIGS. 4C and D show commercially available Sigma Type I collagen. Sigma collagen provided a less dense fibril architecture compared to the pig skin collagen. Scanning electron microscopy was performed according to Voytik-Harbin, et al. Small intestinal submucosa: A tissue-derived extracellular matrix that promotes tissue-specific growth and differentiation of cells in vitro. *Tissue Engineering,* 4:157-174 (1998), incorporated herein by reference. Note that scanning electron microscopy analysis involves fixing and critical point drying and the required processing of the specimens is known to lead to microstructural artifacts. Therefore, this technique alone is not relied on to determine the 3D microstructure of engineered ECMs.

Example 6

Mechanical Behavior Comparison Using Unconfined Compression

Figure 5:
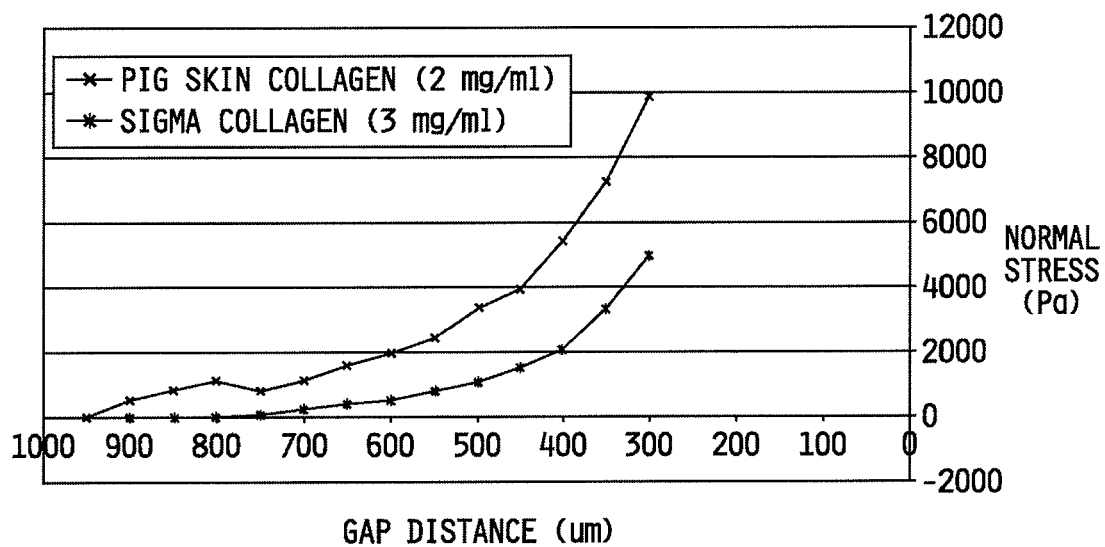
FIG. 5 shows a comparison using a compression test of the mechanical properties (e.g., strength and modulus (stiffness)) of an engineered ECM prepared from pig skin collagen, using the methods described herein, and a commercially available collagen preparation.

FIG. 5 shows the mechanical behavior of a 3D ECM engineered from pig skin collagen (polymerized at 2 mg/ml), prepared in accordance with the methods described herein, and from commercially available Sigma Type I collagen (polymerized at 3 mg/ml). Mechanical behavior was compared using unconfined compression. The specimen was subjected to unconfined compression at a rate of 10 or 20 micrometers/sec using an AR-2000 rheometer (TA Instruments, New Castle, Del.). As shown in FIG. 5, pig skin collagen, prepared in accordance with the methods described herein, surprisingly exhibited as much as 10-20× greater mechanical integrity as commercially available Sigma Type I collagen.

Example 7

Collagen Polymerization Conditions

Briefly, collagen was polymerized by using a 10×PBS, pH 7.4 solution consisting of 1.37M NaCl, 0.027M KCl, 0.081M $Na_2HPO_4$, 0.015M $KH_2PO_4$, 5 mM $MgCl_2$, and 1% w/v glucose. To polymerize collagen, a mixture was made of 1 ml of solubilized collagen in 0.01N HCl, 150 μl 10×PBS, pH 7.4, 150 μl 0.1N NaOH, 100 μl 13.57 mM $CaCl_2$, and 100 μl 0.01 N HCl. The composition was mixed well after each component was added. Polymerization was allowed to proceed at 37° C.

Example 8

Shear Modulus During Polymerization

Mechanical properties of the engineered ECMs prepared with the pig skin collagen, made according to the method described herein, were measured using a TA Instruments (New Castle, Del.) AR-2000 rheometer. Soluble pig skin and commercially available Sigma collagen preparations were adjusted to provide the polymerization conditions described in Example 7 and were placed on the peltier temperature-controlled lower plate at 4° C., and the 40-mm parallel-plate geometry was lowered to a 1-mm gap. The temperature was then raised to 37° C. to initiate polymerization. The peltier heated plate required about 1 minute to stabilize at 37° C. Measurements of shear storage modulus G' of the polymerizing material under controlled-strain oscillatory shear were made every 1 minute under oscillation at 1 Hz and 0.02% strain for a specified time.

Figure 7:
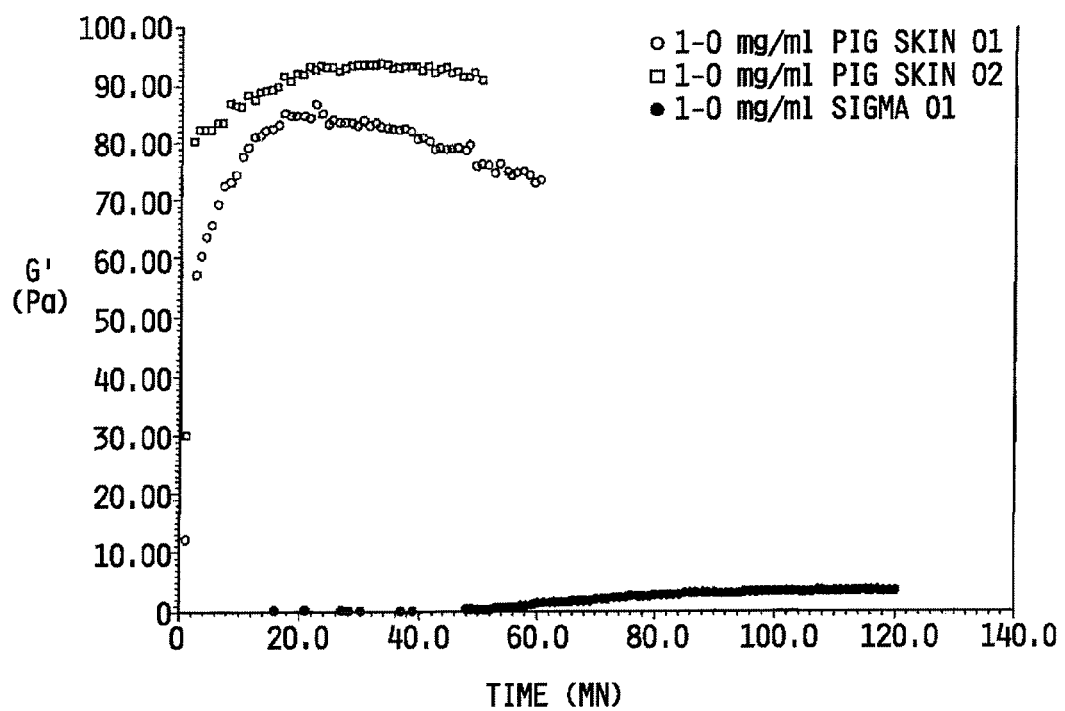
FIG. 7 shows the shear storage (G') modulus during polymerization of an engineered ECM prepared from pig skin collagen, using the methods described herein, compared to a commercially available collagen preparation.

As shown in FIG. 7, for pig skin and Sigma collagen polymerized at the same collagen concentration and using the same polymerization conditions, the shear storage modulus for ECMs prepared from pig skin collagen, according to the methods described herein, is 10 to 40 times greater than that obtained for ECMs prepared from commercially available Sigma collagen.

Example 9

Stem Cell Growth on Collagen ECM

The pig skin collagen preparation, made in accordance with the methods described herein, has been seeded with a number of different cell types, including human mesenchymal stem cells (Clonetics) and a mesenchymal stem cell line derived from the bone marrow of mice (D1, American Type Culture Collection (ATCC)). Experiments have demonstrated that these multi-potential stem cells can be seeded within engineered ECMs prepared from the pig skin collagen and maintain viability. Furthermore, a broader range of fibril microstructures and mechanical properties (stiffness) can be obtained for engineered ECMs prepared from pig skin collagen, according to the methods described herein. The ability to control fibril microstructure and mechanical properties (stiffness) over a broad range is critical to the ability to direct the behavior and differentiation of cells.

Figure 8A:
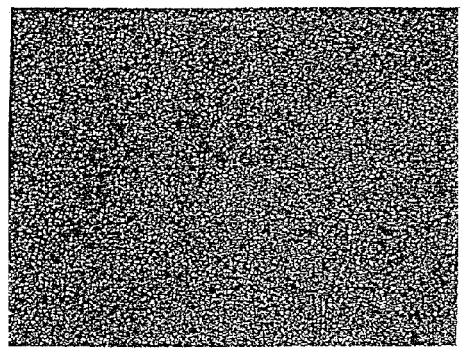
FIGS. 8A and B show the growth of mesenchymal stem cells on an engineered collagen ECM polymerized at 0.5 mg/ml (FIG. 8A) or 3 mg/ml (FIG. 8B) of collagen, and polymerized from pig skin collagen, isolated according to the methods described herein.
Figure 8B:
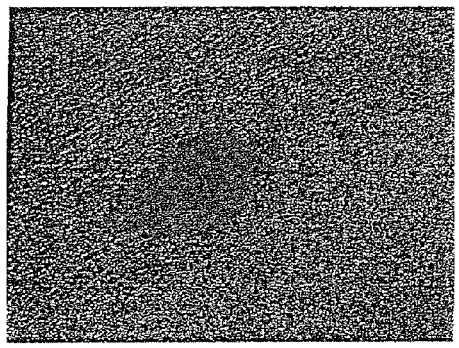

For example, engineered ECMs were prepared using pig skin collagen, prepared according to the methods described herein, or commercially available Sigma collagen preparations at two concentrations, specifically 0.5 mg/ml and 3 mg/ml. These formulations were used to entrap and culture mouse mesenchymal stem cells within a 3D format. Results showed that engineered ECMs of varied microstructures and mechanical properties (stiffness) could be prepared from pig skin collagen. In turn, mouse mesenchymal stem cells cultured within pig skin ECMs of relatively low stiffness (0.5 mg/ml) showed preferential differentiation down the adipogenic pathway (FIG. 8A) while those prepared with relatively high stiffness (3 mg/ml) supported enhanced osteogenic differentiation (FIG. 8B). Compared to ECMs prepared with commercially available Sigma collagen, those prepared from pig skin supported enhanced osteogenesis. The differences in the two preparations to support osteogenic differentiation of multi-potential stem cells can be attributed to differences in ECM microstructure and mechanical properties. Engineered ECMs of increased mechanical integrity (strength and stiffness) are much more readily obtained using the pig skin collagen preparation, made according to the methods described herein. The cells in FIG. 8 A were cultured for periods of time up to 3 weeks in DMEM supplemented with 10% fetal bovine serum, 0.5 mM isobutyl-methylxanthine, 1 μM dexamethasone, 10 μM insulin, 200 μM indomethacin, 0.3 mg/ml glutamine, 100 U/ml penicillin, and 100 μg/ml streptomycin. The cells in FIG. 8 B were cultured for periods of time up to 3 weeks in DMEM supplemented with 10% fetal bovine serum, 0.3 mg/ml glutamine, 100 U/ml penicillin, and 100 μg/ml streptomycin.

Example 10

Glycerol Separation of Oligomer and Monomer Components of Collagen Compositions

Type I collagen isolated from pig skin was solubilized in acetic acid (0.005 M) to achieve a desired collagen concentration (4 mg/ml). An equal volume of 2× solubilization buffer was added (0.06 M phosphate, 0.2 M NaCl, and 1.2 M glycerol, pH 7.0) with mixing. The solution was left to stand at 30° C. for 7 days. At desired times, the solution was then centrifuged at 10,000 rpm and 4° C. for 10 minutes and decanted and the supernatant was retained. The pellet was then resolubilized in 0.1 M acetic acid and the resolubilized pellet and the supernatant were dialyzed against 0.01 M acetic acid and lyophilized to dryness.

Example 11

Analysis of Collagen Fibril Microstructure

Confocal reflection (CRM) microscopy was used to collect high resolution images of ECMs (without cells). Fibril density and fibril diameters were measured from the images to quantify the effect of HA concentration on the collagen fibrillar microstructure. Confocal imaging was performed on a Olympus Fluoview FV1000 confocal system adapted to a IX81 inverted microscope (Olympus, Tokyo, Japan). For the fibril density, confocal image stacks were collected from random locations within independent ECMs for each treatment. The fibril density for each image was calculated in Matlab (Mathworks, Natick, Mass.) as the ratio of fibril volume (voxels containing fibrils) to total volume after binarizing (thresholding) the images. Fibril diameters were measured from the 2D projections of the confocal images in Imaris 5.0 (Bitplane Inc., Saint Paul, Minn.). Each fibril diameter represents the average of 5 diameters measured along the major axis of an individual fibril.

Example 12

Rheometry Protocol

About 1.5 ml of collagen was neutralized according to the Sirius red concentration in a 2 ml eppendorf tube (all reagents were on ice). A balance was used to acquire the proper amount of collagen assuming 1 g=1 ml (a weight within 3 mg is acceptable). The weight was recorded to the nearest mg. Proper amounts of HCL and PBS were added and the tube was shaken moderately. NaOH was added and the tube was shaken moderately. Finally, CaCl and HCL were added and the tube was shaken. The tubes were then centrifuged 10K. The sample was removed and 1 ml of the sample was added to a cold rheometer plate (no bubbles should be allowed into the solution on the plate and excessive condensation should not be allowed on the cold plate). The geometry was spun lightly and the geometry was lowered to a 725 μm gap position (this position correlates to 1 ml). The spinning motion helped to insure that the sample was evenly distributed under the geometry. Once the geometry was at the proper gap, it was verified that the collagen solution extended to the edge of the plate, but not past it. The vapor trap was placed on the plate, and the normal force was zeroed. A reading was then taken.

Example 13

Glycerol Separation of Oligomers and Monomers

Figure 9:
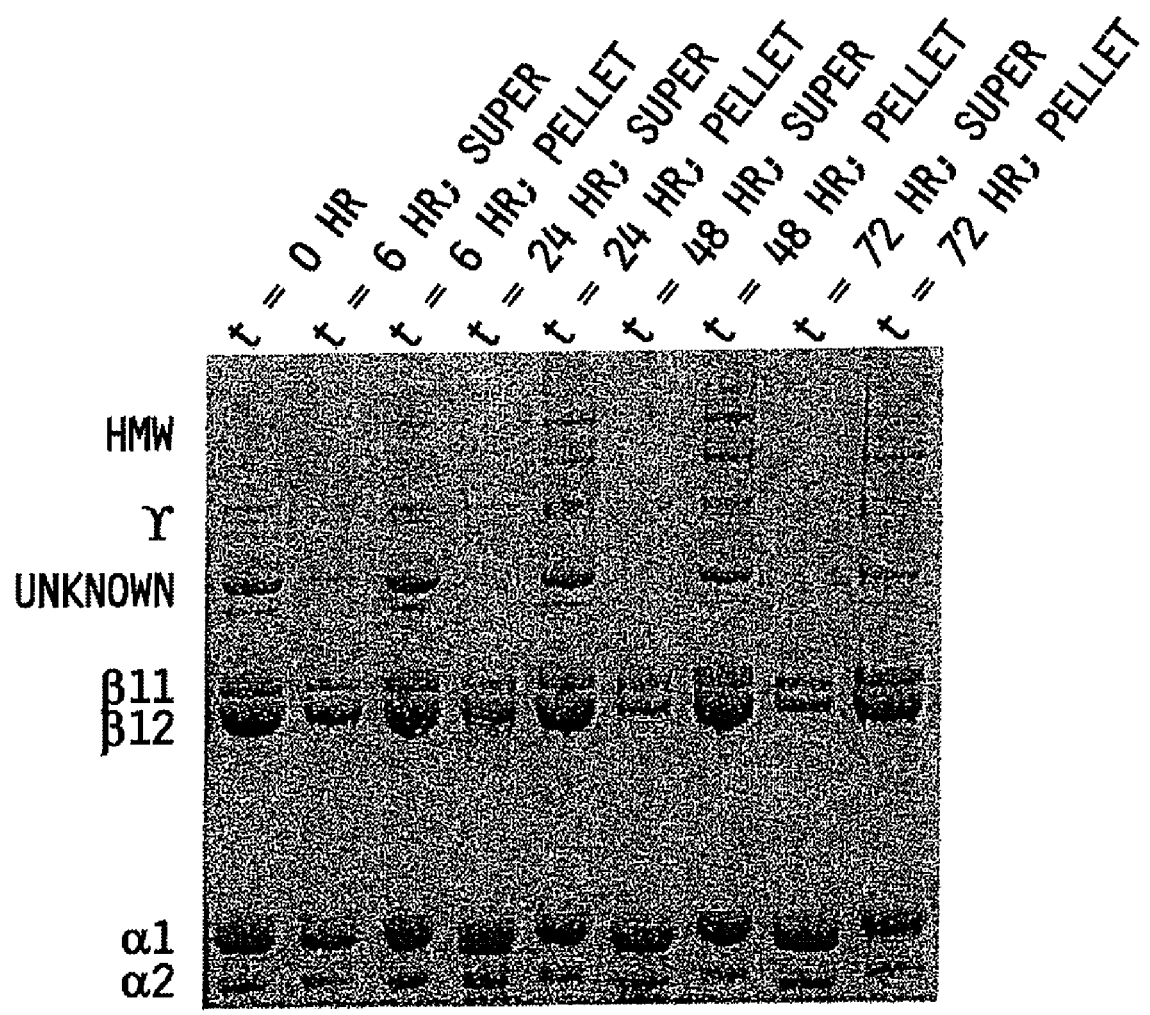
FIG. 9 shows the time-dependent glycerol-based separation of pig skin collagen type I oligomers and monomers. At each time point, the supernatant and pellet represent the monomer-rich and oligomer-rich fractions, respectively.

The glycerol separation was preformed according to the method described in Example 10. FIG. 9 shows the time-dependent glycerol-based separation of pig skin collagen type I oligomers and monomers. At each time point (0, 6, 24, 48, and 72 hours), the supernatant and pellet represent the monomer-rich and oligomer-rich fractions, respectively. By definition collagen monomers represent single collagen molecules and oligomers represent covalently cross-linked monomers (e.g., dimers=2 monomers, trimers=3 monomers, etc.). The results in FIG. 9 show that the pellet is enriched in the higher molecular weight oligomeric collagen molecules.

Example 14

Densitometry Readings after Glycerol-Based Separation of Oligomers and Monomers

Figure 10A:
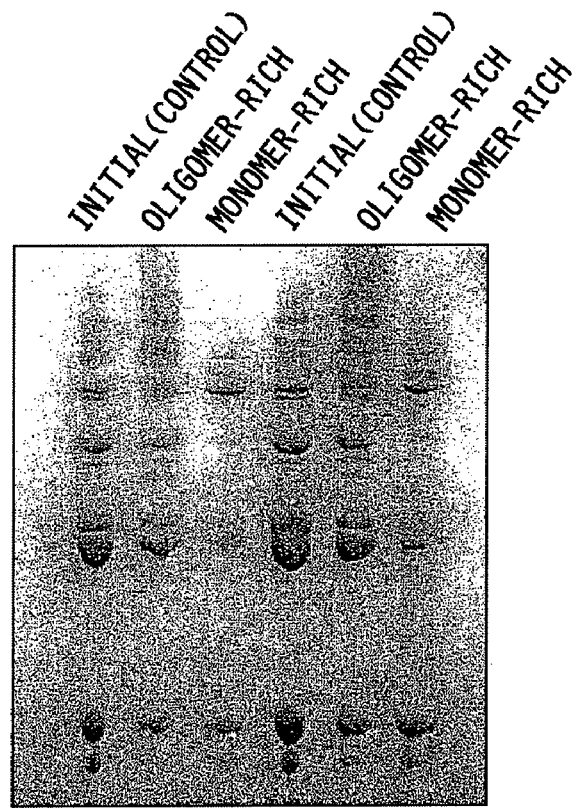
FIGS. 10A and B show glycerol-based separation of pig skin collagen type I oligomers and monomers. Pig skin collagen was polymerized in the presence of glycerol for 7 days. The mixture was centrifuged and the supernatant and pellet retained, dialyzed against dilute acetic acid and lyophilized to dryness. The supernatant and pellet represented monomer- and oligomer-rich collagen compositions, respectively, as determined by SDS-PAGE (4%).
Figure 10B:
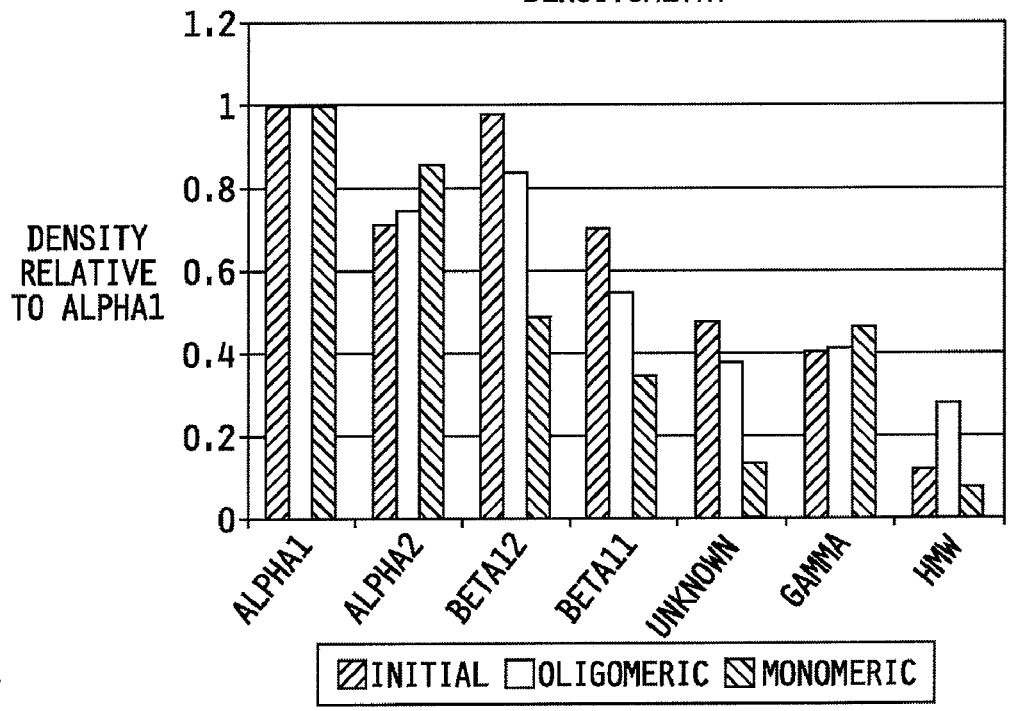

FIG. 10A shows glycerol-based separation of pig skin collagen type I oligomers and monomers. Pig skin collagen was polymerized in the presence of glycerol for 7 days as described in Example 10. The mixture was centrifuged and the supernatant and pellet retained, dialyzed against dilute acetic acid, and lyophilized to dryness. The supernatant and pellet represented monomer- and oligomer-rich collagen compositions, respectively, as determined by SDS-PAGE (4%). FIG. 10A shows the SDS-PAGE gel of the samples and FIG. 10B shows the corresponding densitometry readings. With reference to the labeling of bands shown in FIG. 9, the densitometry readings show a comparison of the oligomer-rich and monomer-rich fraction densitometry readings for individual bands on the SDS-PAGE gel relative to densitometry readings for alpha 1. For the densitometry results, the leftmost bar for each group of 3 bars is the initial (before glycerol separation) densitometry reading for each band relative to alpha 1 in the initial isolated collagen preparation, the middle bar for each group of 3 bars is the desitometry reading for each band in the oligomer-rich fraction after glycerol-based separation relative to alpha 1, and the rightmost bar for each group of 3 bars is the desitometry reading for each band in the monomer-rich fraction after glycerol-based separation relative to alpha 1. The results show that for known oligomers (e.g., β12), the oligomers are found mainly in the pellet after glycerol-based separation. SDS-PAGE analysis was performed as described in Example 2.

Example 15

CNBr Peptide Analysis of Collagen Oligomers

Figure 11:
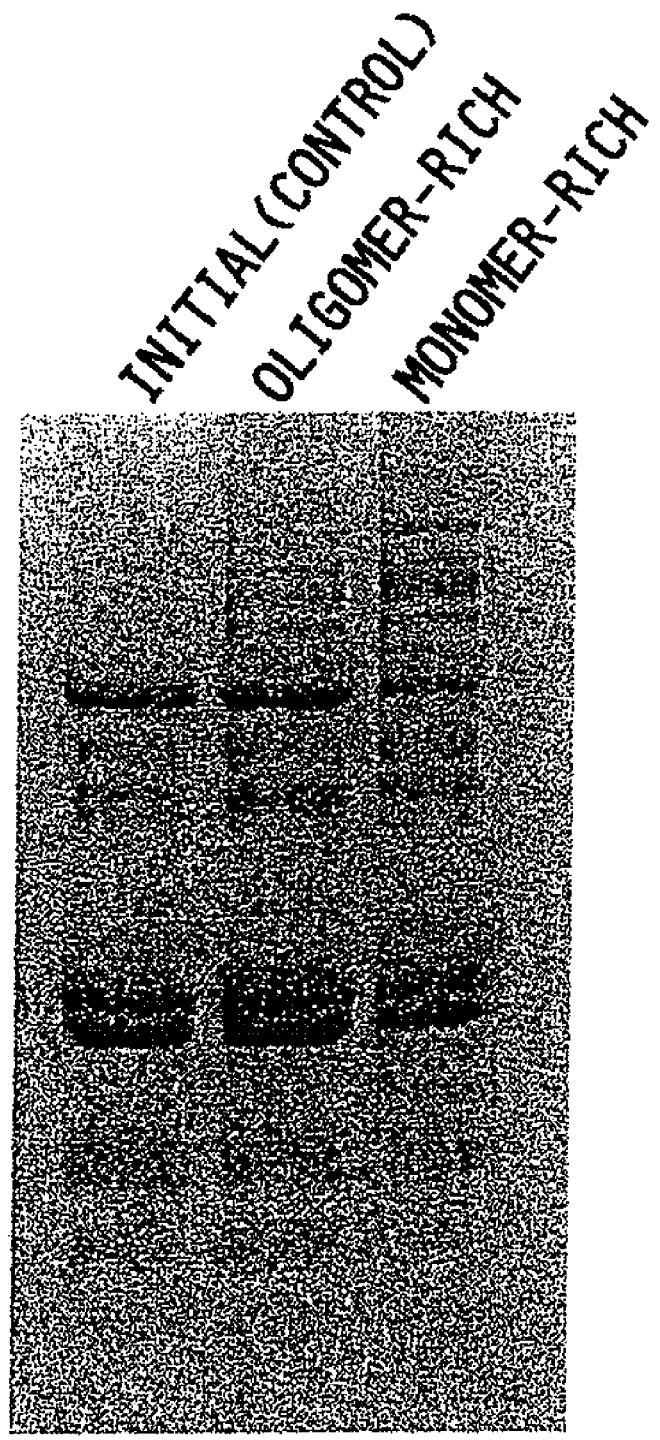
FIG. 11 shows SDS-PAGE (12%) analysis of CNBr peptide maps of collagen preps in which oligomer:monomer content is varied. Upon CNBr digestion, collagen preps yield distinct peptide fingerprints indicating distinct molecular compositions and cross-linked moieties.

FIG. 11 shows SDS-PAGE (12%) analysis of CNBr peptide maps of collagen preps in which oligomer:monomer content is varied. Upon CNBr digestion, collagen preps yielded distinct peptide fingerprints indicating distinct molecular compositions and cross-linked moieties. SDS-PAGE analysis and CNBr peptide analysis were performed as described in Example 3.

Example 16

Polymerization Kinetics of Oligomeric Collagen

Figure 12A:
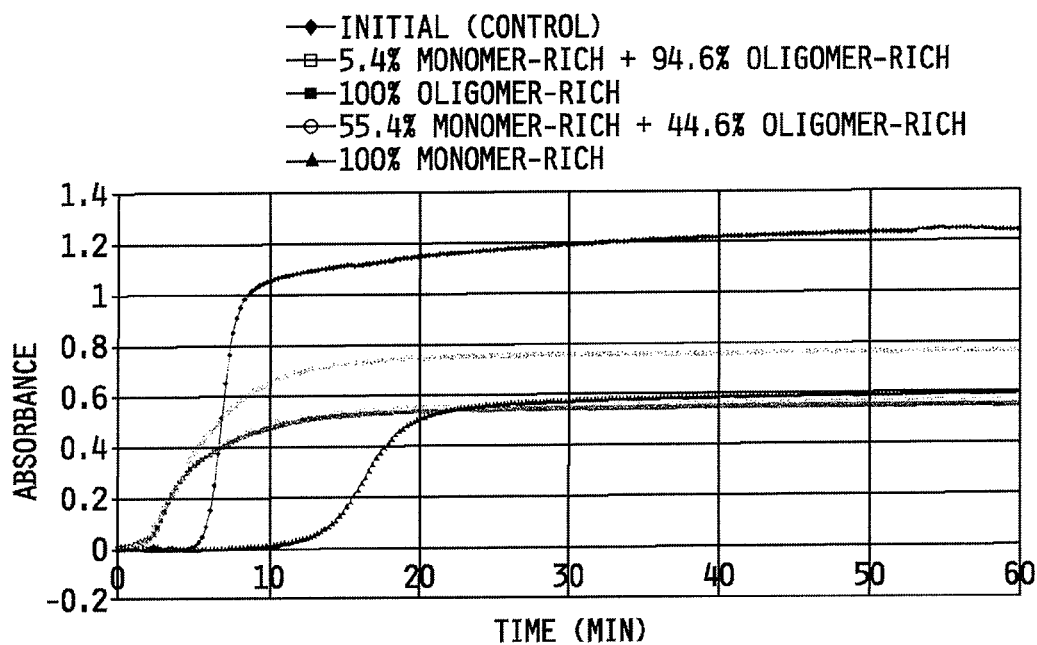
FIG. 12A shows $A_{405}$ vs. time.
Figure 12B:
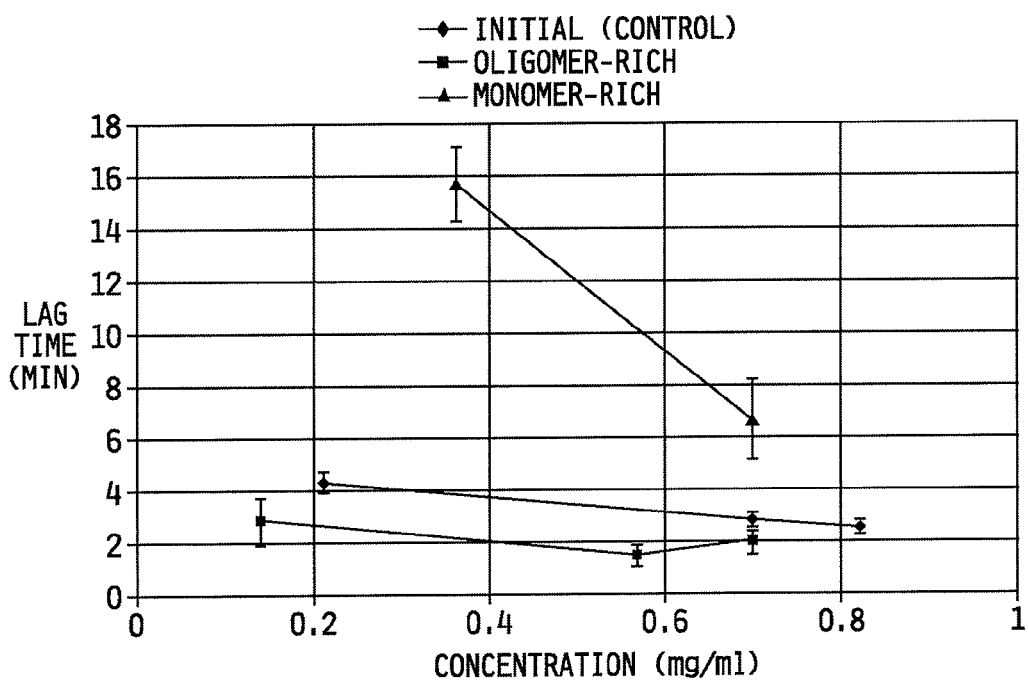
FIGS. 12 A-B show the oligomer:monomer content of pig skin collagen preparation affects polymerization (self-assembly) kinetics. An increase in oligomer content decreases lag time (FIG. 12 B) and increases the rate of polymerization (FIG. 12 A).

Polymerization kinetics were measured as described in Example 3. FIGS. 12 A-B show the oligomer:monomer content of pig skin collagen preparation affects polymerization (self-assembly) kinetics. An increase in oligomer content decreases lag time (FIG. 12 B) and increases the rate of polymerization (FIG. 12 A). FIG. 12A shows $A_{405}$ vs time. In FIG. 12 A, the uppermost line is the control (0.7 mg/ml collagen) which is the resuspended collagen pellet after collagen isolation, but prior to glycerol separation. The lowest line is 100% monomer-rich collagen. The middle lines from top to bottom are 1.) 5.4% monomer-rich collagen and 94.6% oligomer-rich collagen, 2.) 100% oligomer-rich collagen, and 3.) 55.4% monomer rich+44.6% oligomer-rich collagen.

Example 17

Mechanical Behavior of Extracellular Matrices Prepared with Oligomeric Collagen

Figure 13:
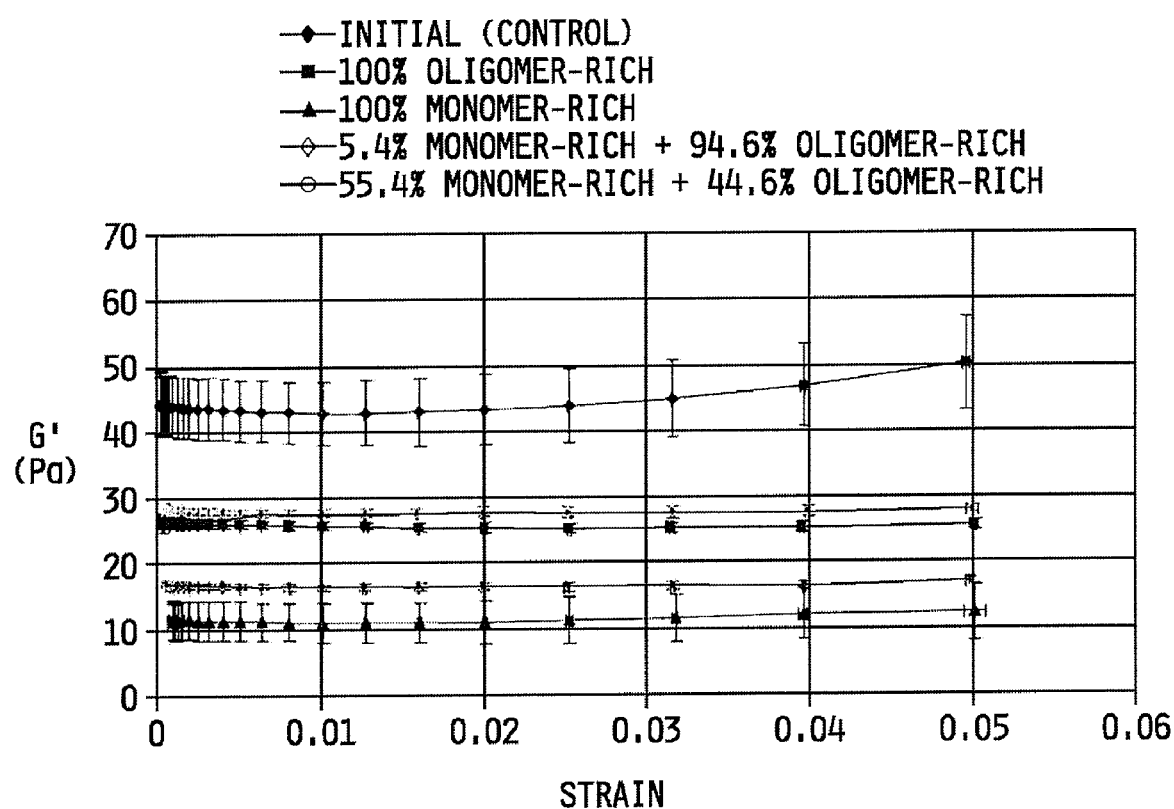
FIG. 13 shows the comparison of mechanical behavior of 3D engineered ECMs prepared with pig skin collagen preps of varied monomer:oligomer content. The shear storage modulus (G') provides a measure of the stiffness of solid (elastic) components. Results show that G' or stiffness of matrices increases with oligomer content.

FIG. 13 shows the results of an assay done to compare mechanical behavior of 3D engineered matrices prepared with pig skin collagen preps of varied monomer:oligomer content. The shear storage modulus (G') provides a measure of the stiffness of the solid (elastic) components. The results in FIG. 13 show that the shear storage modulus (G'; stiffness) of matrices increases with oligomer content. The top line is the control. The bottom line is 100% monomer-rich collagen. The middle lines are (from top to bottom) 5.4% monomer-rich collagen and 94.6% oligomer-rich collagen, 100% oligomer-rich collagen, and 55.4% monomer rich+44.6% oligomer-rich collagen.

Example 18

Mechanical Behavior of Extracellular Matrices Prepared with Oligomeric Collagen

Figure 14:
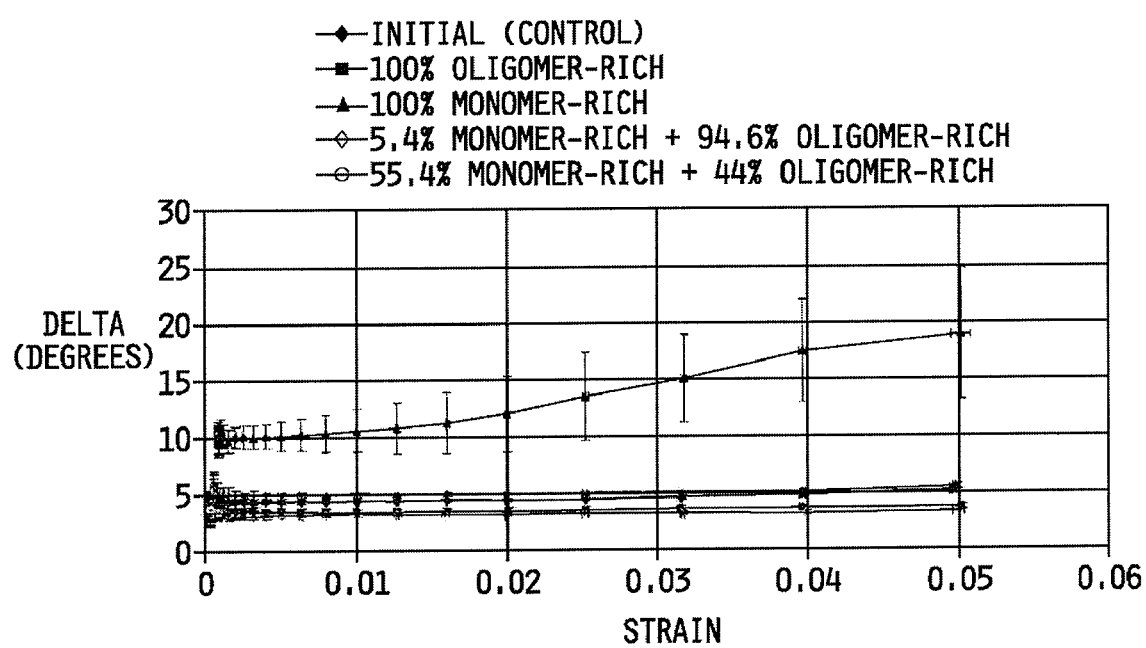
FIG. 14 shows the comparison of mechanical behavior of 3D engineered ECMs prepared with pig skin collagen preps of varied monomer:oligomer content. An increase in delta as a function of strain as observed with the monomer-rich preparation indicates more fluid-like (viscous) behavior.

FIG. 14 shows the comparison of mechanical behavior of 3D engineered matrices prepared with pig skin collagen preps of varied monomer:oligomer content. An increase in delta as a function of strain as observed with the monomer-rich preparation (uppermost line) indicates more fluid-like (viscous) behavior.

Example 19

Mechanical Behavior of Extracellular Matrices Prepared with Oligomeric Collagen

Figure 15:
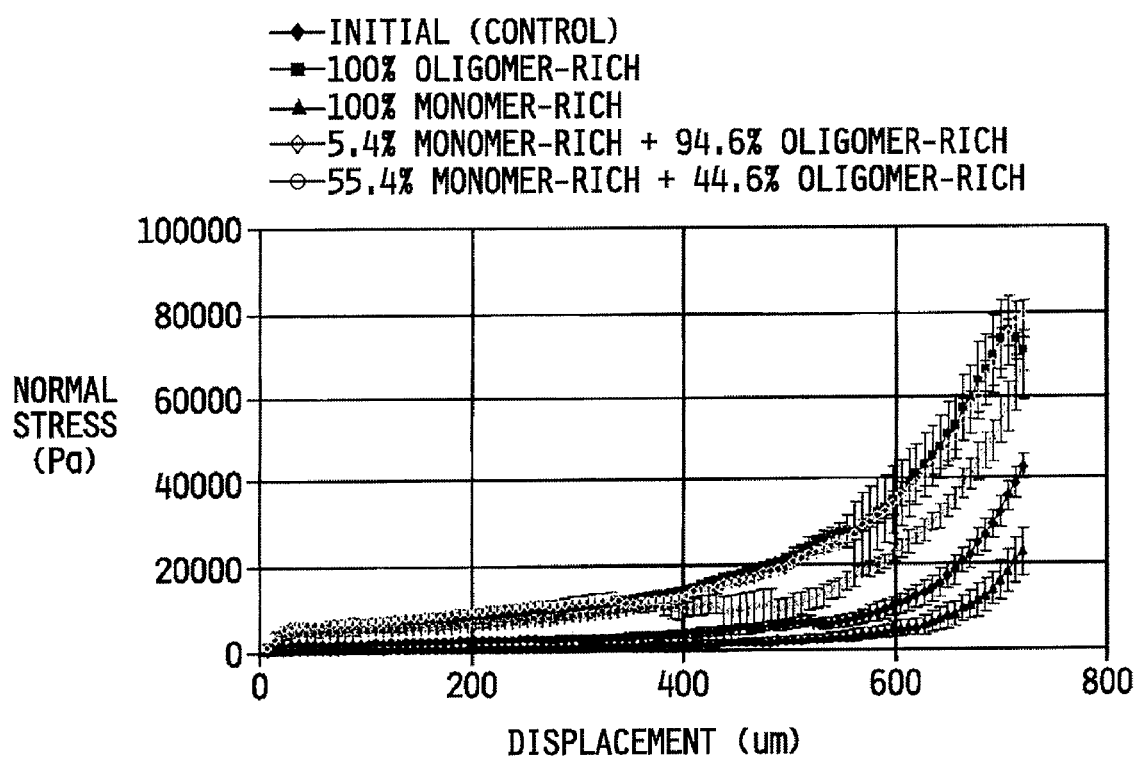
FIG. 15 shows the comparison of mechanical behavior of 3D engineered ECMs prepared with pig skin collagen preps of varied monomer:oligomer content. Matrices produced with collagen preps consisting of higher oligomer content show increased compressive modulus (stiffness) and failure strength.

FIG. 15 shows a comparison of mechanical behavior of 3D engineered matrices prepared with pig skin collagen preps of varied monomer:oligomer content. Matrices produced with collagen preps consisting of higher oligomer content show increased compressive stiffness. The bottom line is monomer-rich collagen. The next line towards the top is the control. The top three lines are, from top to bottom, 100% oligomer-rich collagen, 5.4% monomer-rich collagen and 94.6% oligomer-rich collagen, and 55.4% monomer rich+44.6% oligomer-rich collagen.

Example 20

Mechanical Behavior of Extracellular Matrices Prepared with Oligomeric Collagen

Figure 16:
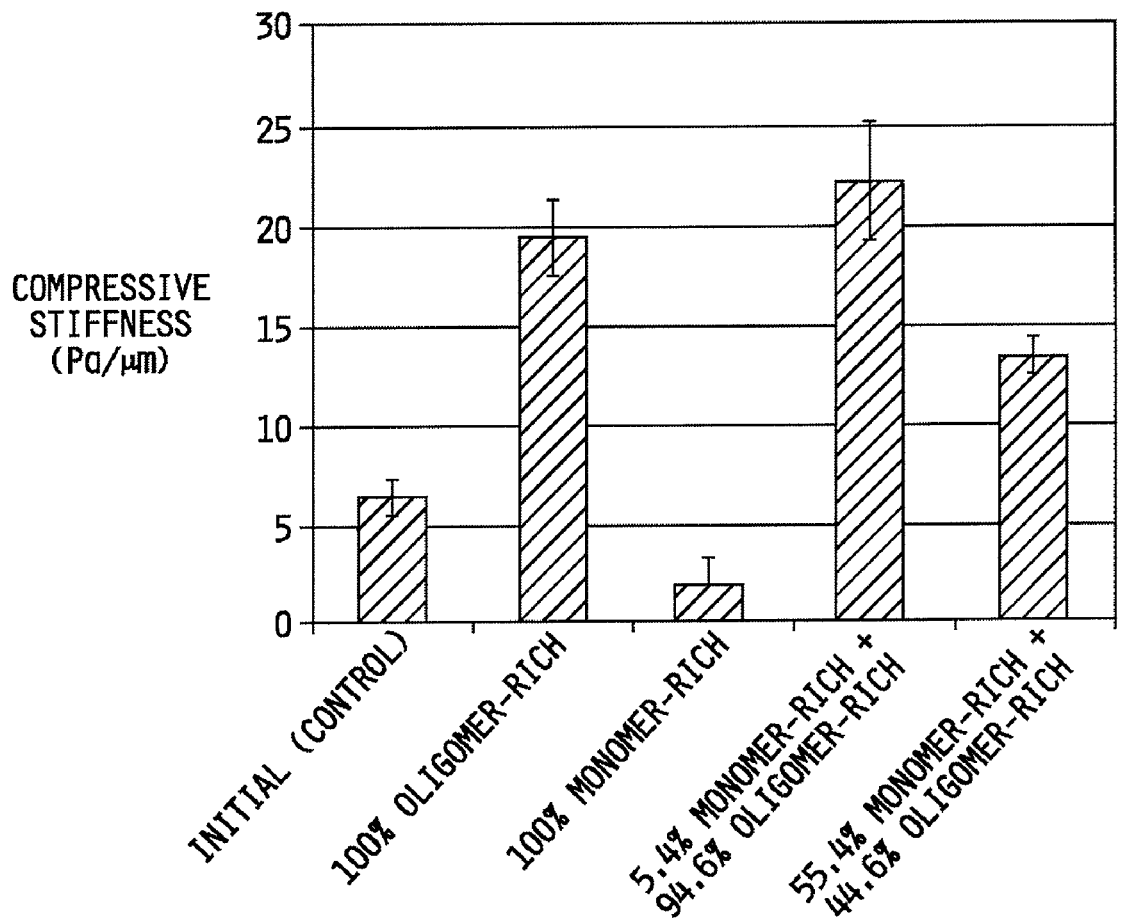
FIG. 16 shows the compressive modulus (stiffness) values as a function of the oligomer:monomer content of the pig skin collagen preparation.

FIG. 16 shows the results of an assay done to determine the compressive stiffness values as a function of the oligomer:monomer content of the pig skin collagen preparation. The results show that stiffness increases with increasing oligomer content.

Example 21

Figure 17:
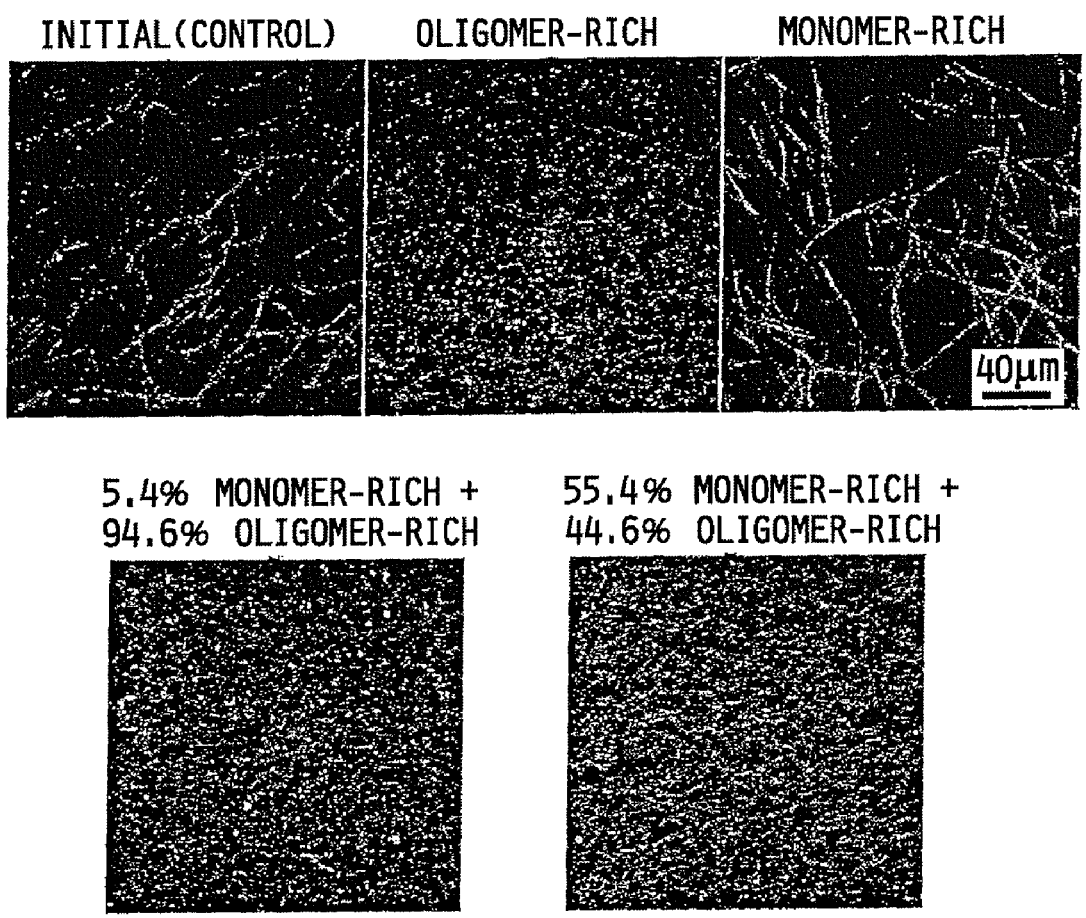
FIG. 17 shows the effects of oligomer content on the 3D collagen fibril microstructure of engineered ECMs.

Confocal Microscopy to Visualize Engineered Matrices Made with Varying Oligomer Content FIG. 17 shows the effects of oligomer content on the 3D collagen fibril microstructure of engineered matrices. The matrices were prepared with the percentages of oligomers and monomers shown. The oligomer-rich and monomer-rich preparations were 100% oligomer-rich and 100% monomer-rich, respectively. Confocal microscopy was performed as described in Example 4.

Example 22

Figure 18:
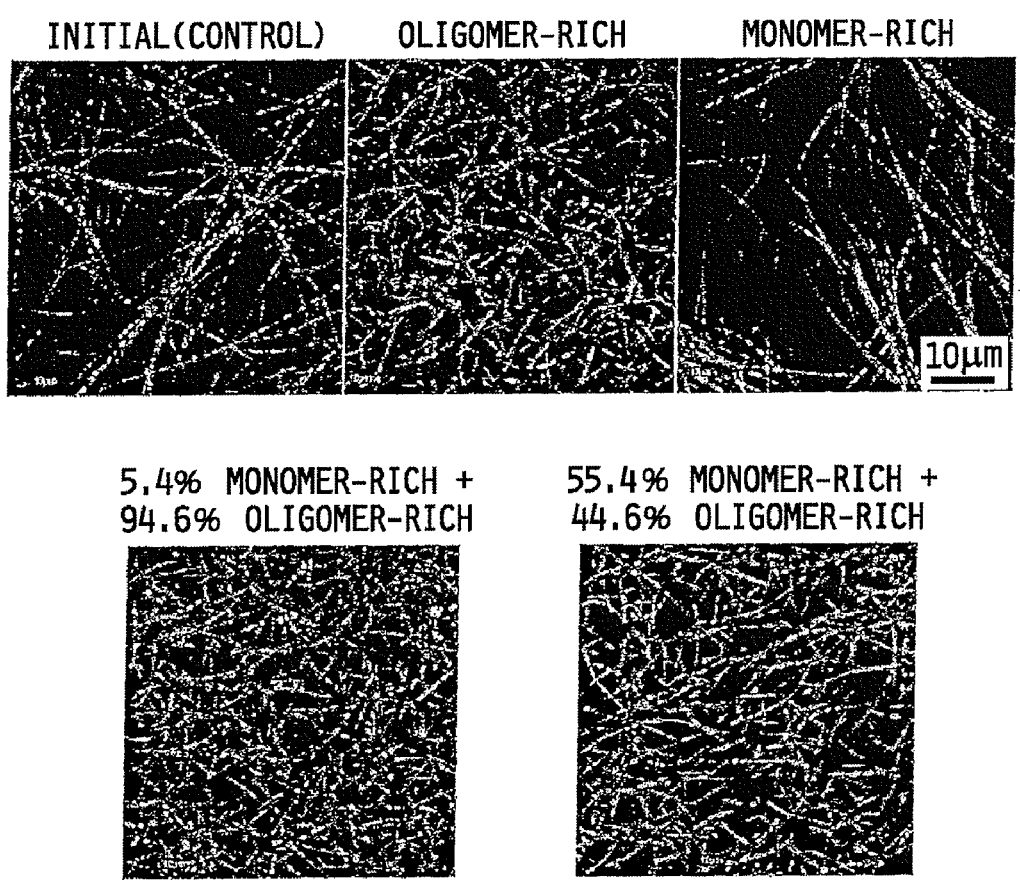
FIG. 18 shows the effects of oligomer content on the 3D collagen fibril microstructure of engineered ECMs.

Confocal Microscopy to Visualize Engineered Matrices Made with Varying Oligomer Content FIG. 18 shows the effects of oligomer content on the 3D collagen fibril microstructure of engineered matrices. The matrices were prepared with the percentages of oligomers and monomers shown. The oligomer-rich and monomer-rich preparations were 100% oligomer-rich and 100% monomer-rich, respectively. Confocal microscopy was performed as described in Example 4.

Example 23

SDS-PAGE Analysis of Collagen Preparations

Figure 19:
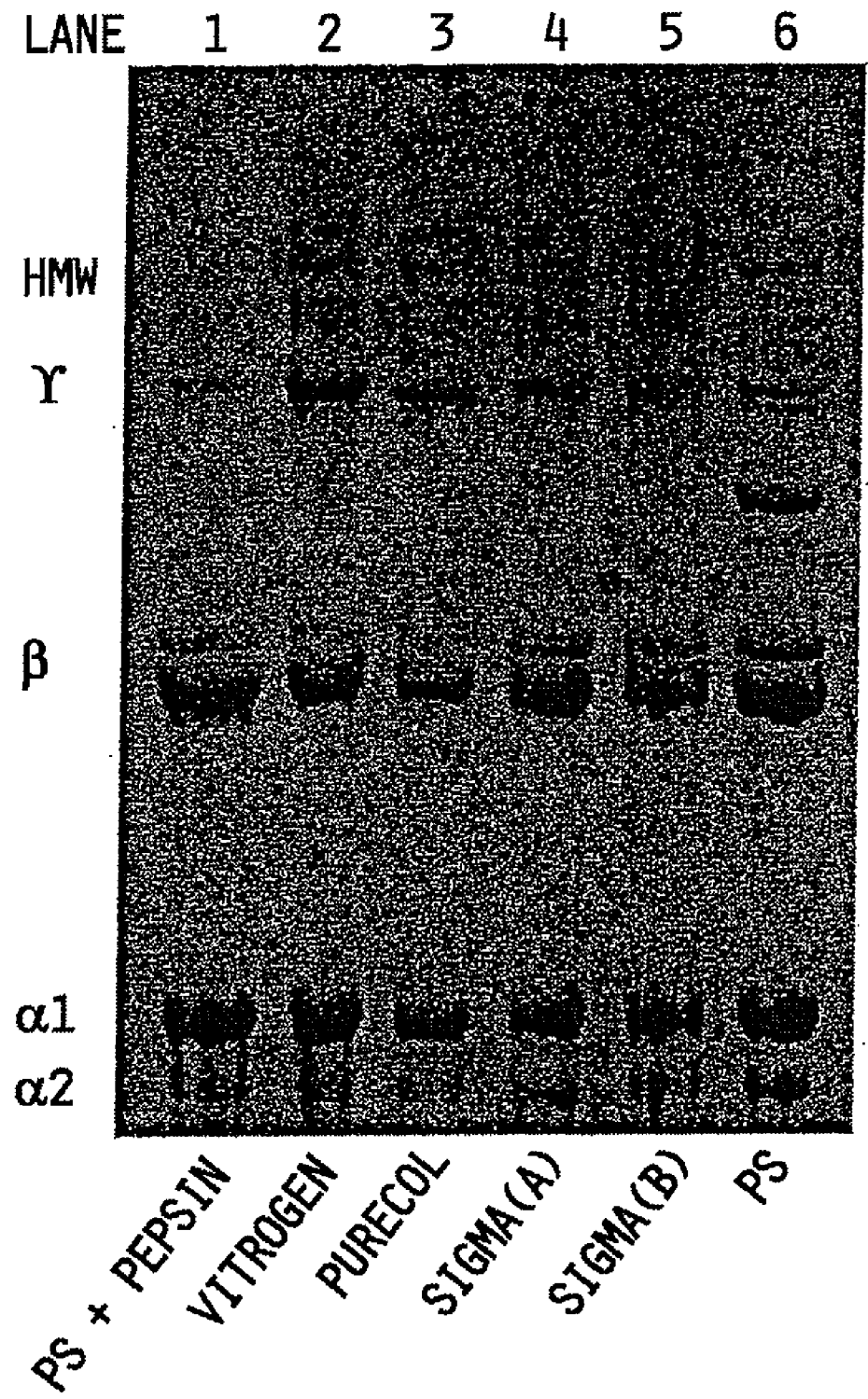
FIG. 19 shows the compositional analysis of different collagen preparations as determined using SDS-PAGE (4%). Results show that the pig skin collagen preparation uniquely contains collagen oligomers that run intermediate between commonly identified dimeric (β) and trimeric (γ) forms of collagen. Upon pepsin treatment of pig skin collagen, the content of unique collagen oligomers as other higher molecular weight collagen species is significantly reduced. Lane 1=PS+pepsin (acid solubilized type I collagen from pig skin posted-treated with pepsin); Lane 2=Vitrogen (pepsin solubilized type I collagen from calf skin); Lane 3=PureCol (pepsin solubilized type I collagen from calf skin); Lane 4=(Sigma, A) acid solubilized type I collagen from calf skin, Lot A; Lane 5=(Sigma, B) acid solubilized type I collagen from calf skin, Lot B; Lane 6=PS (acid solubilized type I collagen from pig skin).

FIG. 19 shows the compositional analysis of different collagen preparations as determined using SDS-PAGE (4%). The results in FIG. 19 show that the pig skin collagen preparation uniquely contains collagen oligomers that run intermediate between commonly identified dimeric ($\beta$) and trimeric ($\gamma$) forms of collagen. Upon pepsin treatment of pig skin collagen, the content of unique collagen oligomers as well as other higher molecular weight collagen species was significantly reduced. Lane 1=PS+pepsin (acid solubilized type I collagen from pig skin posted-treated with pepsin); Lane 2=Vitrogen (pepsin solubilized type I collagen from calf skin); Lane 3=PureCol (pepsin solubilized type I collagen from calf skin); Lane 4=(Sigma, A) acid solubilized type I collagen from calf skin, Lot A; Lane 5=(Sigma, B) acid solubilized type I collagen from calf skin, Lot B; Lane 6=PS (acid solubilized type I collagen from pig skin). SDS-PAGE analysis and CNBr peptide analysis were performed as described in Example 3.

Example 24

Polymerization Kinetics of Different Collagen Preparations

Figure 20:
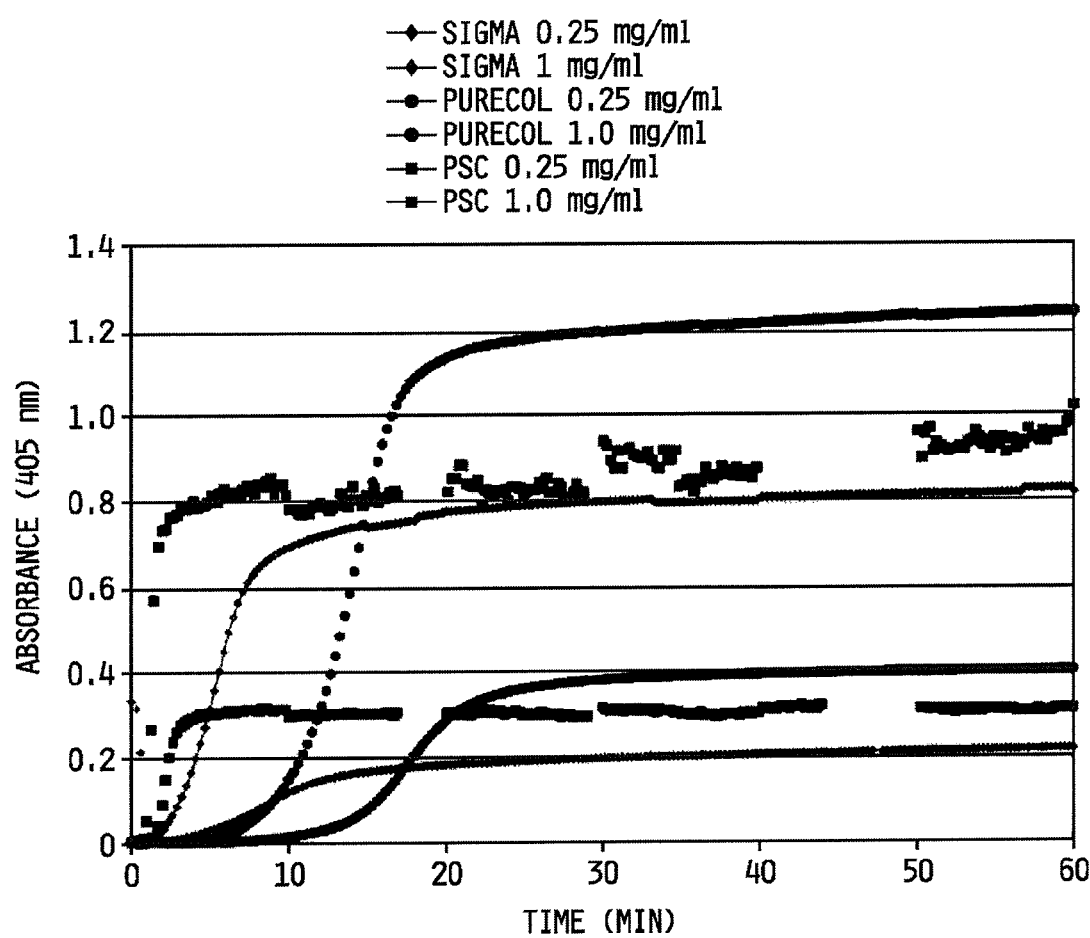
FIG. 20 shows the kinetics of polymerization for the different collagen preparations as determined using spectrophotometric-based turbidity assay. Results show that the polymerization kinetics of collagen is highly dependent upon the collagen preparation. More specifically, polymerization of pig skin collagen shows a decreased lag phase and an increased rate of polymerization (slope of growth phase).

FIG. 20 shows the kinetics of polymerization for the different collagen preparations as determined using the spectrophotometric-based turbidity assay described in Example 3. Results show that the polymerization kinetics of collagen is highly dependent upon the collagen preparation. More specifically, polymerization of pig skin collagen shows a decreased lag phase and an increased rate of polymerization (slope of growth phase). Pig skin collagen (0.25 mg/ml) and pig skin collagen (1.0 mg/ml) are the lower and upper leftmost lines, respectively. Sigma collagen (0.25 mg/ml) and Sigma collagen (1.0 mg/ml) are the lowest line and the line where the third highest absorbance was achieved, respectively. PureCol (0.25 mg/ml) and PureCol (1.0 mg/ml) are the line with the greatest lag time and the line where the highest absorbance was achieved, respectively.

Example 25

Polymerization of Different Collagen Preparations

Figure 21:
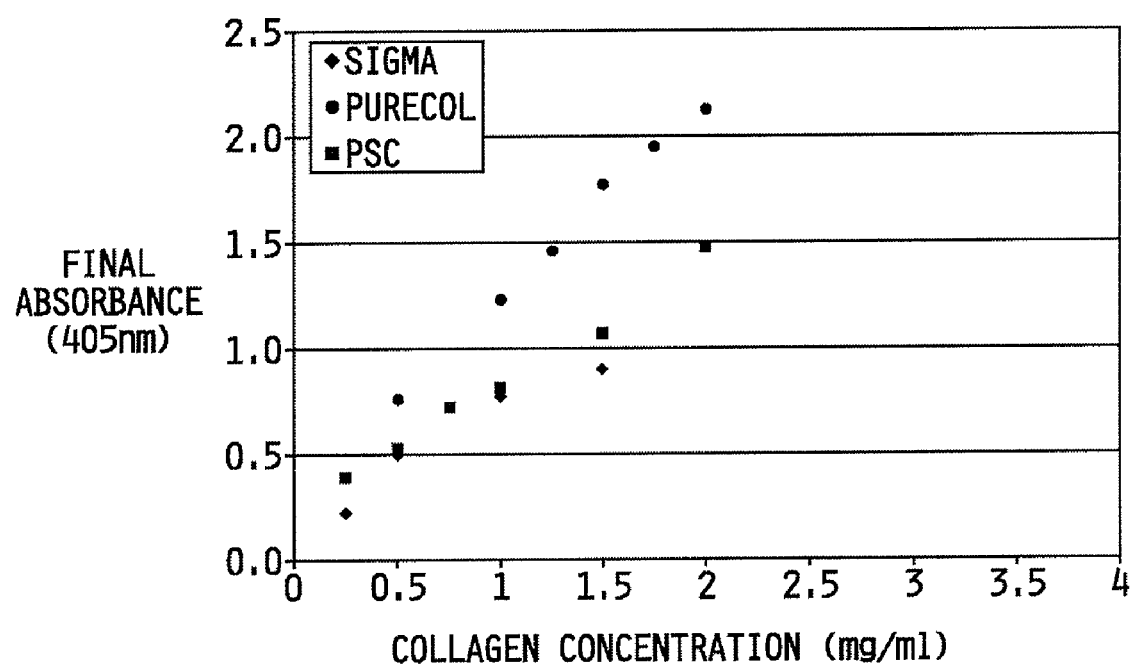
FIG. 21 shows the comparison of final absorbance (405 nm) values for different collagen preparations as determined from spectrophometric based turbidity assay. Results represent average of last 10 absorbance values.

FIG. 21 shows a comparison of final absorbance (405 nm) values for different collagen preparations as determined from

Example 26

Confocal Microscopy to Visualize Different Engineered Matrices

Figure 22:
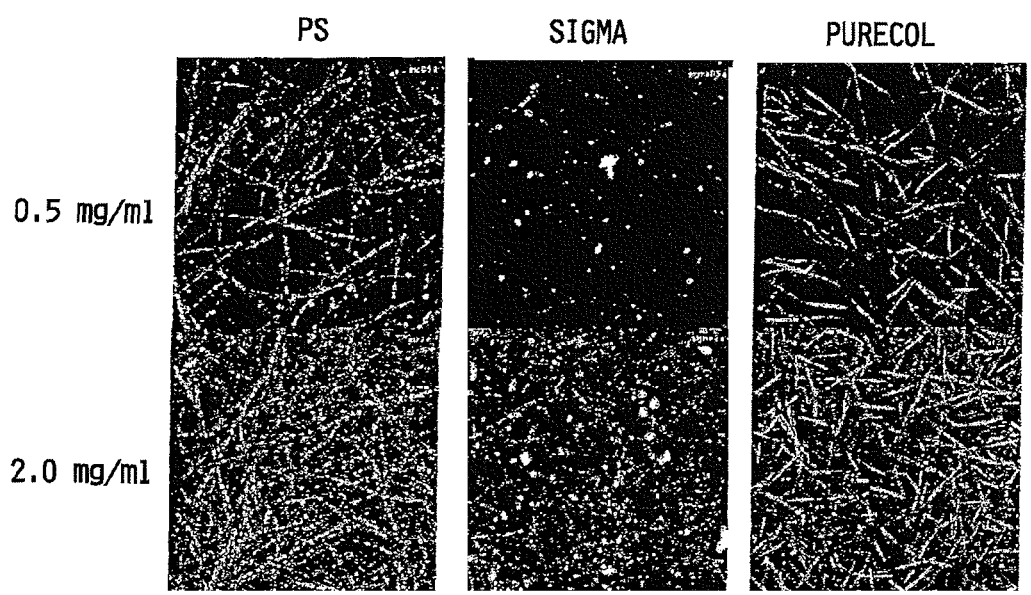
FIG. 22 shows the collagen fibril microstructure of 3D engineered ECMs prepared with different purified type I collagen sources. Each collagen preparation was polymerized at two different concentrations (0.5 mg/ml and 2 mg/ml) using the same reaction conditions. Images represent 2D projections of 3D image stacks as collected using confocal reflection microscopy. Results show that the collagen fibril microstructure of 3D engineered ECMs is highly dependent upon the collagen preparation.

FIG. 22 shows the collagen fibril microstructure of 3D engineered ECMs prepared with different purified type I collagen sources. Each collagen preparation was polymerized at two different concentrations (0.5 mg/ml and 2 mg/ml) using the same reaction conditions. Images represent 2D projections of 3D image stacks as collected using confocal reflection microscopy as described in Example 4. The results show that the collagen fibril microstructure of 3D engineered ECMs is highly dependent upon the collagen preparation.

Example 27

Figure 23:
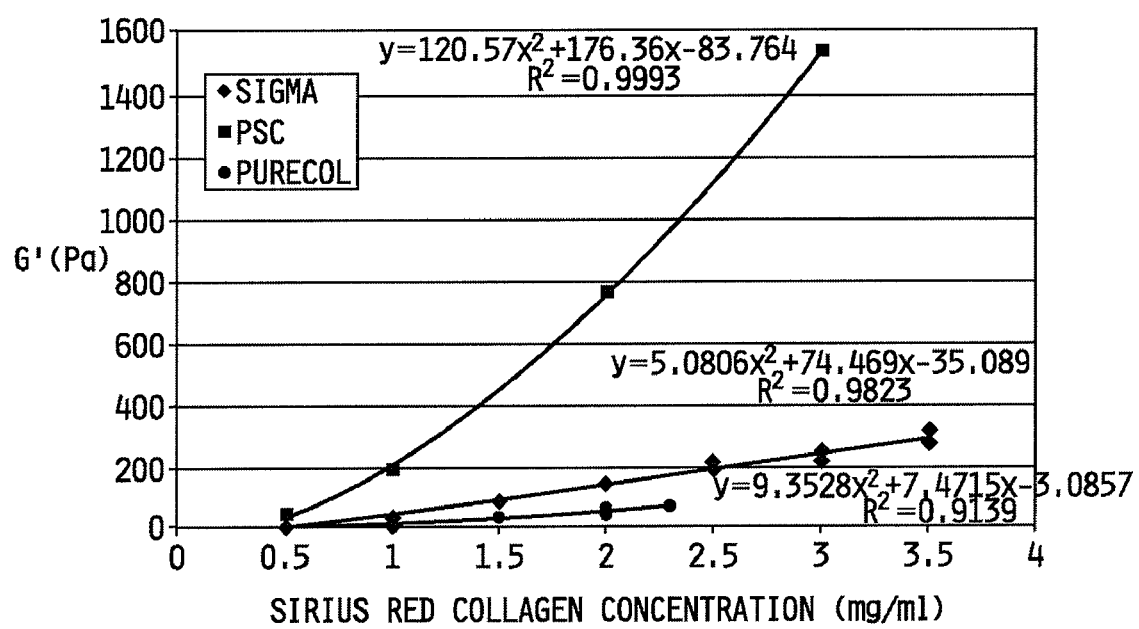
FIG. 23 shows the comparison of mechanical behavior 3D engineered ECMs prepared with different collagen preparations and tested in oscillatory shear. The storage modulus (G') provides a measure of the stiffness of the solid (elastic) components. Results show that G' or stiffness of matrices prepared with pig skin collagen are significantly greater than those obtained with the commercial collagen preparations (PureCol and Sigma).

Mechanical Behavior of Extracellular Matrices Prepared with Different Collagen Preparations FIG. 23 shows the comparison of mechanical behavior of 3D engineered ECMs prepared with different collagen preparations and tested in oscillatory shear. The storage modulus (G') provides a measure of the stiffness of the solid (elastic) components. Results show that the stiffness of matrices prepared with pig skin collagen are significantly greater than those obtained with the commercial collagen preparations (PureCol and Sigma).

Example 28

Figure 24A:
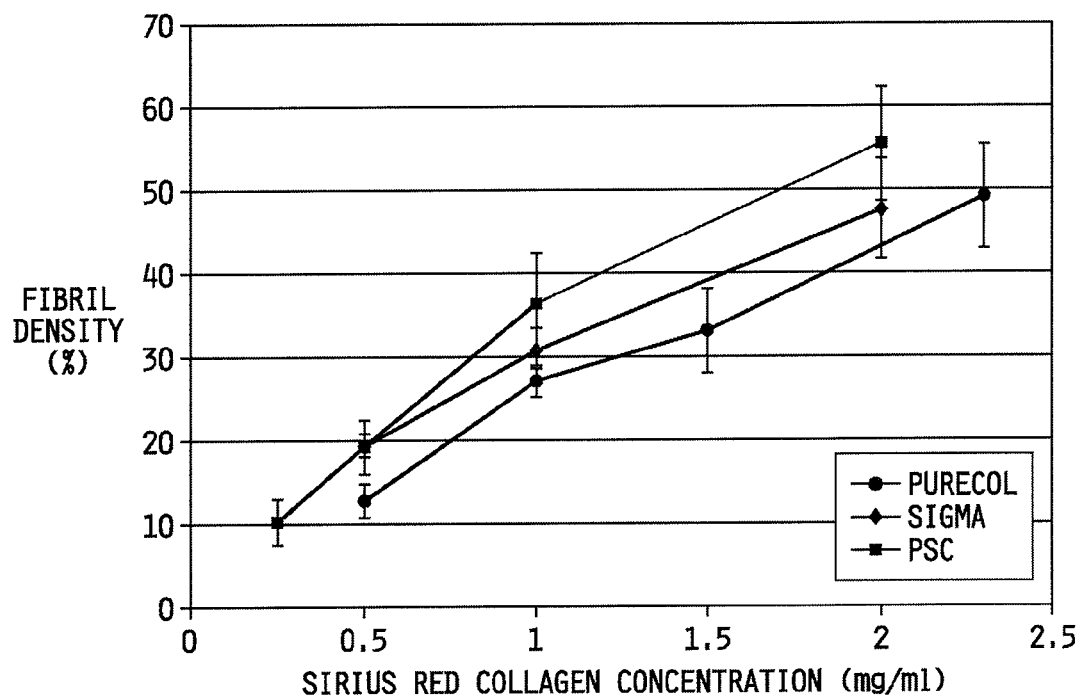
FIGS. 24A-B show a comparison of collagen sources.
Figure 24B:
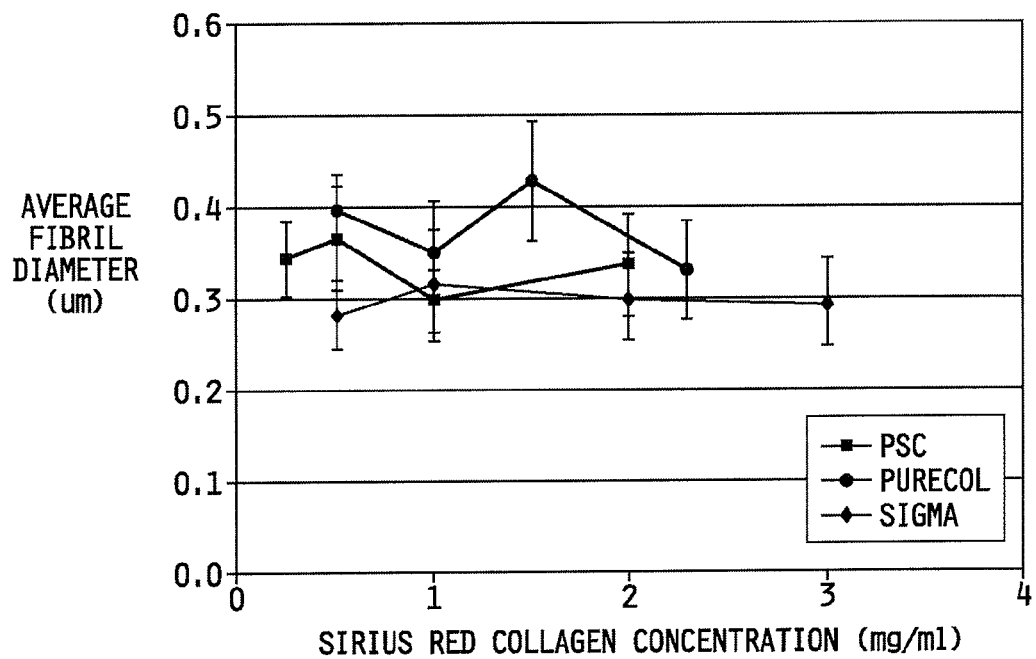

Mechanical Behavior of Extracellular Matrices Prepared with Different Collagen Preparations FIGS. 24A-B show a comparison of mechanical behaviors of engineered matrices prepared with different collagen sources. FIG. 24 A shows microstructural analysis of engineered ECMs using confocal reflection microscopy (fibril density vs. collagen concentration). FIG. 24 B shows microstructural analysis of engineered ECMs using confocal reflection microscopy (average fibril diameter vs. collagen concentration). Collagen stiffness (G' vs. fibril density) and rheometric analysis of mechanical properties (G' (Pa) vs. collagen concentration) were also performed. Confocal microscopy was as described in Example 4.

Example 29

Effect of Oligomer Content on Polymerization Efficiency

Table 1 shows the effect of oligomer content on polymerization efficiency. Polymerization was assayed as described in Example 4. The collagen that remained in solution as polymerized versus non-polymerized collagen was determined based on a Sirius Red assay. The results in table 1 show that oligomer-rich collagen polymerizes more efficiently than monomer-rich collagen.

TABLE 1

Effect of Oligomer Content on Polymerization Efficiency.

| Collagen Preparation | Collagen Concentration (mg/mL) | % Polymerized (t = 1 hour) |
| --- | --- | --- |
| Initial (Control) | 0.82 | 100% |
|  | 0.7 | 100% |
|  | 0.21 | 100% |
| Oligomer-Rich | 0.7 | 100% |
|  | 0.57 | 100% |
|  | 0.14 | 100% |
| Monomeric-Rich | 0.7 | 86.6% |
|  | 0.36 | 81.4% |
|  | 0.09 | 58.4% |

Example 30

Half-Polymerization Times for Different Collagen Preparations

Table 1 shows the $t\ \frac{1}{2}$'s for polymerization for different collagen preparations. Polymerization was assayed as described in Example 4. The results in Table 2 show that oligomer-rich pig skin collagen polymerizes with a $t\ \frac{1}{2}$ that is much lower than Sigma collagen or PureCol. A $t\ \frac{1}{2}$ is the half-time required to achieve maximal absorbance.

TABLE 2

Comparison of half-polymerization times ($t_{1/2}$) for different collagen preparations as determined from spectrophometric based turbidity assay.

| Collagen Preparation | $t_{1/2}$ (minutes) |
| --- | --- |
| PSC (Acid Solubilized Type I Collagen from Pig Skin) | 1-1.5 |
| PureCol (Pepsin Solubilized Type I Collagen from Calf Skin) | 13-17 |
| Sigma (Acid Solubilized Type I Collagen from Calf Skin) | 5-9 |

What is claimed is:

1. An engineered matrix comprising a percentage of collagen oligomers based on total isolated collagen used to make the engineered matrix, wherein the percentage of collagen oligomers is about 40% to about 100% in dry weight based on the total collagen used to make the matrix and wherein the collagen is isolated from a tissue naturally enriched with collagen oligomers.

2. The matrix of claim 1 wherein the collagen oligomers are isolated from a diseased tissue.

3. The matrix of claim 1 wherein the collagen oligomers are obtained by isolating and then chemically cross-linking collagen.

4. The matrix of claim 1 wherein the engineered matrix further comprises isolated collagen monomers.

5. A graft composition comprising an engineered matrix comprising collagen oligomers wherein the matrix has a percentage of collagen oligomers based on total isolated collagen used to make the engineered matrix, and wherein the percentage of collagen oligomers is about 40% to about 100% in dry weight based on the total collagen used to make the matrix and wherein the collagen oligomers are obtained from a tissue naturally enriched with collagen oligomers.

6. The graft composition of claim 5 wherein the collagen oligomers are isolated from a diseased tissue.

7. The graft composition of claim 5 wherein the collagen oligomers are obtained by isolating and then chemically cross-linking collagen.

8. The graft composition of claim 5 wherein the engineered matrix further comprises a percentage of collagen monomers based on total isolated collagen used to make the engineered matrix.

9. The matrix of claim 1 wherein the percentage of collagen oligomers is about 70% to about 100%.

10. The matrix of claim 1 wherein the matrix is sterilized with peracetic acid.

11. The matrix of claim 1 wherein the tissue naturally enriched with collagen oligomers is selected from the group consisting of placental tissue, ovarian tissue, animal tail tissue, and skin tissue.

12. The matrix of claim 11 wherein the tissue naturally enriched with collagen oligomers is porcine skin.

13. The matrix of claim 1 wherein the oligomers are generated by crosslinking.

14. The matrix of claim 1 wherein the matrix further comprises cells.

15. The matrix of claim 1 wherein the matrix further comprises a glycoprotein, a glycosaminoglycan, or a proteoglycan.

16. The graft composition of claim 5 wherein the percentage of collagen oligomers is about 70% to about 100%.

17. The graft composition of claim 5 wherein the graft is sterilized with peracetic acid.

18. The graft composition of claim 5 wherein the tissue naturally enriched with collagen oligomers is selected from the group consisting of placental tissue, ovarian tissue, animal tail tissue, and skin tissue.

19. The graft composition of claim 18 wherein the tissue naturally enriched with collagen oligomers is porcine skin.

20. The graft composition of claim 5 wherein the collagen oligomers are generated by crosslinking.

21. The graft composition of claim 5 wherein the graft is implantable.

22. The graft composition of claim 5 wherein the graft is injectable.

23. The graft composition of claim 5 wherein the graft composition further comprises cells.

24. The graft composition of claim 5 wherein the graft composition further comprises a glycoprotein, a glycosaminoglycan, or a proteoglycan.

* * * * *

UNITED STATES PATENT AND TRADEMARK OFFICE
CERTIFICATE OF CORRECTION

| | | |
|---|---|---|
| PATENT NO. | : 8,084,055 B2 | Page 1 of 1 |
| APPLICATION NO. | : 11/903326 | |
| DATED | : December 27, 2011 | |
| INVENTOR(S) | : Sherry L. Voytik-Harbin et al. | |

It is certified that error appears in the above-identified patent and that said Letters Patent is hereby corrected as shown below:

In column 1, lines 10-13, please replace the text "Research relating to this invention was supported in part by the U.S. Government under Grant No. EB000165 awarded from the National Institutes of Health. The U.S. Government has certain rights in this invention." with the text -- This invention was made with government support under Grant No. EB000165 awarded from the National Institutes of Health. The government has certain rights in the invention. --

Signed and Sealed this
Seventeenth Day of April, 2012

David J. Kappos
*Director of the United States Patent and Trademark Office*